(12) United States Patent
Badawi et al.

(10) Patent No.: US 12,740,888 B2
(45) Date of Patent: Sep. 22, 2026

(54) TREATMENT APPARATUS AND METHODS

(71) Applicant: Sight Sciences, Inc., Menlo Park, CA (US)

(72) Inventors: Paul Badawi, Menlo Park, CA (US); Scott Harshman, Woodinville, WA (US)

(73) Assignee: Sight Sciences, Inc., Menlo Park, CA (US)

( * ) Notice: Subject to any disclaimer, the term of this patent is extended or adjusted under 35 U.S.C. 154(b) by 5 days.

(21) Appl. No.: 16/523,078

(22) Filed: Jul. 26, 2019

(65) Prior Publication Data

US 2021/0022914 A1 Jan. 28, 2021

(51) Int. Cl.
*A61F 7/00* (2006.01)

(52) U.S. Cl.
CPC ...... *A61F 7/007* (2013.01); *A61F 2007/0004* (2013.01); *A61F 2007/0086* (2013.01); *A61F 2007/0093* (2013.01)

(58) Field of Classification Search
CPC .............. A61F 2007/0004; A61F 7/007; A61F 2007/0071; A61F 2007/0086; A61F 2007/0088; A61F 2007/0093; A61F 7/02; A61F 2007/0225; A61F 2007/0226; A61F 2007/0244; A61F 2007/0246; A61F 2007/0247; A61F 2007/0263
See application file for complete search history.

(56) References Cited

U.S. PATENT DOCUMENTS

| | | | |
|---|---|---|---|
| 2,001,862 | A | 5/1935 | Carter |
| 2,108,934 | A | 2/1938 | Albright |
| 2,635,175 | A | 4/1953 | Hodge |
| 3,075,527 | A | 1/1963 | Bechtold |

(Continued)

FOREIGN PATENT DOCUMENTS

| | | |
|---|---|---|
| CN | 202313590 | 7/2012 |
| CN | 103417306 | 12/2013 |

(Continued)

OTHER PUBLICATIONS

Blackie, Caroline A. et al., "Inner Eyelid Surface Temperature as a Function of Warm Compress Methodology," *Optometry and Vision Science*, vol. 85, No. 8, pp. 675-683, Aug. 2008.

(Continued)

*Primary Examiner* — Bradford C. Blaise
(74) *Attorney, Agent, or Firm* — Levine Bagade Han LLP

(57) ABSTRACT

Treatment apparatus and methods are described for treating the meibomian glands of a subject. The system may generally include a substrate layer having one or more heating elements incorporated, a ductile layer attached in proximity to the substrate layer and configured to conform and retain a shape of the heating strip to an anatomy of an underlying region of skin of an eyelid of a subject, and a protective layer attached in proximity to the ductile layer. The system may further include a controller which is programmable for a treatment therapy and which is in communication with the substrate layer via a connecting cable which transmits electrical energy to the substrate layer which receives the (Continued)

electrical energy and emits thermal energy which is conducted throughout the strip via the ductile layer to the underlying region of skin.

36 Claims, 12 Drawing Sheets

(56) References Cited

U.S. PATENT DOCUMENTS 3,173,419 A 3/1965 Dublier et al.
3,589,369 A 6/1971 Alksnis
4,096,864 A 6/1978 Kletschka et al.
4,261,364 A 4/1981 Haddad et al.
4,325,254 A 4/1982 Svacina et al.
4,867,146 A 9/1989 Krupnick et al.
4,930,317 A 6/1990 Klein
4,962,761 A 10/1990 Golden
5,097,829 A 3/1992 Quisenberry
5,164,987 A 11/1992 Raven
5,169,384 A 12/1992 Bosniak et al.
5,643,336 A 7/1997 Lopez-Claros
5,860,985 A 1/1999 Anschutz
6,066,164 A 5/2000 Macher et al.
6,074,414 A 6/2000 Haas et al.
6,155,995 A 12/2000 Lin
6,193,741 B1 2/2001 Heavenridge et al.
D441,081 S 4/2001 Mueller
6,238,427 B1 5/2001 Matta
6,409,746 B1 6/2002 Igaki et al.
6,416,534 B1 7/2002 Montagnino et al.
6,511,446 B1 1/2003 Wu
6,860,880 B2 3/2005 Treat et al.
6,908,195 B2 6/2005 Fuller, Jr.
D507,054 S 7/2005 Mueller et al.
D507,055 S 7/2005 Mueller et al.
D507,350 S 7/2005 Mueller et al.
D507,651 S 7/2005 Mueller et al.
6,923,988 B2 8/2005 Patel et al.
D511,573 S 11/2005 Mueller et al.
D513,323 S 12/2005 Mueller et al.
7,069,084 B2 6/2006 Yee
7,108,694 B2 9/2006 Miura et al.
7,211,070 B2 5/2007 Soroudi
7,229,468 B2 6/2007 Wong, Jr. et al.
D613,408 S 4/2010 Gausmann et al.
D614,303 S 4/2010 Gausmann et al.
D614,774 S 4/2010 Gausmann et al.
D617,443 S 6/2010 Grenon et al.
7,758,190 B2 7/2010 Korb et al.
7,833,205 B2 11/2010 Grenon et al.
D638,128 S 5/2011 Prokop et al.
7,976,573 B2 7/2011 Korb et al.
7,981,095 B2 7/2011 Grenon et al.
7,981,145 B2 7/2011 Korb et al.
7,981,146 B2 7/2011 Korb et al.
7,981,147 B2 7/2011 Korb et al.
7,988,294 B2 8/2011 Korb et al.
8,007,524 B2 8/2011 Korb et al.
8,025,689 B2 9/2011 Korb et al.
8,506,539 B2 8/2013 Guillon et al.
8,535,363 B1 9/2013 Lewis
8,685,073 B2 4/2014 Korb et al.
8,915,253 B2 12/2014 Grenon et al.
8,950,405 B2 2/2015 Grenon et al.
8,960,204 B2 2/2015 Samain et al.
9,510,972 B2 12/2016 Badawi
9,642,743 B2 5/2017 Badawi
9,724,230 B2 8/2017 Badawi
9,844,459 B2 12/2017 Badawi
10,052,226 B2 8/2018 Badawi et al.
10,772,758 B2 9/2020 Badawi
10,925,765 B2 2/2021 Badawi
10,973,680 B2 4/2021 Badawi et al.
11,285,040 B2 3/2022 Badawi et al.
12,257,181 B2 3/2025 Badawi et al.
12,263,115 B2 4/2025 Badawi et al.
12,336,930 B2 6/2025 Badawi
2002/0117495 A1 8/2002 Kochman et al.
2002/0180929 A1 12/2002 Tseng et al.
2003/0167556 A1 9/2003 Kelley
2003/0236487 A1 12/2003 Knowlton
2004/0044384 A1* 3/2004 Leber .................. A61N 5/0619 607/96
2004/0116990 A1 6/2004 Agarwal et al.
2004/0237969 A1 12/2004 Fuller
2005/0119629 A1 6/2005 Soroudi
2005/0159775 A1 7/2005 Reynolds
2005/0187502 A1 8/2005 Krempel et al.
2006/0018953 A1 1/2006 Guillon et al.
2006/0069420 A1 3/2006 Rademacher et al.
2006/0136022 A1 6/2006 Wong et al.
2006/0154642 A1 7/2006 Scannell
2006/0200052 A1 9/2006 Lin
2006/0219701 A1 10/2006 Kil
2006/0235497 A1 10/2006 Zanotti
2007/0016255 A1 1/2007 Korb et al.
2007/0060988 A1 3/2007 Grenon et al.
2007/0282012 A1 12/2007 Kinoshita et al.
2008/0039749 A1 2/2008 Kopanic et al.
2008/0039769 A1 2/2008 Peyman
2008/0081999 A1 4/2008 Gravely et al.
2008/0109053 A1 5/2008 Grenon et al.
2008/0114421 A1 5/2008 Korb et al.
2008/0114423 A1 5/2008 Grenon et al.
2008/0114424 A1 5/2008 Grenon et al.
2008/0132978 A1 6/2008 Korb et al.
2008/0132987 A1 6/2008 Westlund et al.
2008/0269850 A1 10/2008 Dodo
2009/0020521 A1 1/2009 Blaszczykiewicz et al.
2009/0048590 A1 2/2009 Conrad et al.
2009/0123886 A1 5/2009 Vaska
2009/0137533 A1 5/2009 Adkins, Jr.
2009/0149925 A1 6/2009 MacDonald et al.
2009/0168019 A1 7/2009 Tuan
2009/0199571 A1 8/2009 Creech et al.
2009/0312823 A1 12/2009 Patience et al.
2010/0010598 A1 1/2010 Igaki et al.
2010/0114086 A1 5/2010 Deem et al.
2010/0172567 A1 7/2010 Prokoski
2010/0174501 A1 7/2010 Myadam
2010/0198282 A1 8/2010 Rogers
2010/0217360 A1 8/2010 Henriksson et al.
2010/0267751 A1 10/2010 Beals et al.
2010/0286654 A1 11/2010 Dos Santos et al.
2011/0046581 A1 2/2011 Linder
2011/0081333 A1 4/2011 Shantha et al.
2011/0198282 A1 8/2011 Chu et al.
2011/0275410 A1 11/2011 Caffey et al.
2012/0062840 A1 3/2012 Ballou et al.
2012/0191164 A1 7/2012 Gander et al.
2012/0213840 A1 8/2012 Lim
2012/0222192 A1 9/2012 Carey et al.
2013/0046367 A1 2/2013 Chen
2013/0083184 A1 4/2013 Yogesan et al.
2013/0172790 A1 7/2013 Badawi
2013/0172829 A1 7/2013 Badawi
2013/0281893 A1 10/2013 Yang
2013/0288196 A1 10/2013 Gordon
2014/0052198 A1* 2/2014 Mohn ...................... A61F 7/00 607/3
2014/0276248 A1 9/2014 Hall et al.
2014/0303694 A1 10/2014 Timme et al.
2014/0316314 A1 10/2014 Schubert
2014/0330129 A1 11/2014 Grenon et al.
2015/0024339 A1 1/2015 Calderon
2015/0025545 A1 1/2015 Grenon et al.
2015/0202417 A1 7/2015 Abreu
2015/0216725 A1 8/2015 Badawi et al.
2016/0045755 A1 2/2016 Chun et al.
2016/0100977 A1* 4/2016 Lee ........................ A61F 7/007 607/109
2016/0106576 A1 4/2016 Badawi et al.
2016/0106775 A1 4/2016 Alster et al.
2016/0317379 A1 11/2016 Mosaddegh

(56) References Cited

U.S. PATENT DOCUMENTS

| | | | | |
|---|---|---|---|---|
| 2017/0014300 | A1* | 1/2017 | Dippo | A61F 7/034 |
| 2017/0079834 | A1 | 3/2017 | Badawi | |
| 2017/0079840 | A1 | 3/2017 | Badawi | |
| 2017/0087009 | A1 | 3/2017 | Badawi et al. | |
| 2017/0165106 | A1 | 6/2017 | Badawi | |
| 2017/0188805 | A1 | 7/2017 | Pradeep | |
| 2017/0273823 | A1 | 9/2017 | Novkov et al. | |
| 2017/0304110 | A1 | 10/2017 | Badawi | |
| 2018/0060556 | A1 | 3/2018 | Fujino | |
| 2018/0071140 | A1* | 3/2018 | Sheydin | A61N 5/0625 |
| 2018/0200494 | A1 | 7/2018 | Gatrall et al. | |
| 2018/0344512 | A1 | 12/2018 | Badawi | |
| 2019/0274873 | A1* | 9/2019 | Schoeggler | A61F 7/007 |
| 2020/0078032 | A1 | 3/2020 | Nanda et al. | |
| 2020/0078211 | A1 | 3/2020 | Badawi et al. | |
| 2020/0188169 | A1 | 6/2020 | McMahon | |
| 2021/0052216 | A1 | 2/2021 | Badawi | |
| 2021/0128058 | A1 | 5/2021 | Habib | |
| 2021/0169682 | A1* | 6/2021 | Alvarez | A61F 13/00051 |
| 2021/0177647 | A1 | 6/2021 | Badawi | |
| 2021/0177648 | A1 | 6/2021 | Badawi et al. | |
| 2022/0168136 | A1 | 6/2022 | Badawi et al. | |
| 2023/0079255 | A1 | 3/2023 | DeAyala | |
| 2024/0238119 | A1 | 7/2024 | Takakuwa | |
| 2025/0177198 | A1 | 6/2025 | Badawi et al. | |
| 2025/0228702 | A1 | 7/2025 | Badawi | |
| 2025/0288458 | A1 | 9/2025 | Badawi | |
| 2025/0352055 | A1 | 11/2025 | Park et al. | |
| 2025/0352059 | A1 | 11/2025 | Park et al. | |
| 2026/0130791 | A1 | 5/2026 | Badawi et al. | |

FOREIGN PATENT DOCUMENTS

| | | |
|---|---|---|
| CN | 203493672 | 3/2014 |
| CN | 203564408 | 4/2014 |
| CN | 205234758 | 5/2016 |
| CN | 205568977 | 9/2016 |
| CN | 107510545 | 12/2017 |
| DE | 29920352 | 3/2000 |
| JP | 1995-185017 | 7/1995 |
| JP | 3071816 | 9/2000 |
| JP | 2003-093431 | 4/2003 |
| JP | 2007-000520 | 1/2007 |
| JP | 2007-185017 | 7/2007 |
| JP | 2007-229175 | 9/2007 |
| JP | 3170844 | 10/2011 |
| JP | 2015-503417 | 2/2015 |
| JP | 2015-527122 | 9/2015 |
| JP | 2016-522711 | 8/2016 |
| JP | 2017-533074 | 11/2017 |
| JP | 2020-199386 | 12/2020 |
| KR | 2003-01311 | 1/2003 |
| KR | 2010-0002818 | 3/2010 |
| WO | WO 1994/011739 | 5/1994 |
| WO | WO 1999/020213 | 4/1999 |
| WO | WO 2000/069506 | 11/2000 |
| WO | WO 2002/067688 | 9/2002 |
| WO | WO 2004/006801 | 11/2004 |
| WO | WO 2005/067907 | 7/2005 |
| WO | WO 2006/099413 | 9/2006 |
| WO | WO 2007/102362 | 9/2007 |
| WO | WO 2008/085162 | 7/2008 |
| WO | WO 2008/100647 | 8/2008 |
| WO | WO 2011/116306 | 9/2011 |
| WO | WO 2013/103413 | 7/2013 |
| WO | WO 2016/070134 | 5/2016 |
| WO | WO 2017/100608 | 6/2017 |
| WO | WO 2018/156022 | 8/2018 |
| WO | WO 2020/055634 | 3/2019 |
| WO | WO 2021/026154 | 2/2021 |
| WO | WO 2025/239981 | 11/2025 |

OTHER PUBLICATIONS

Bron, A.J. et al., "Functional Aspects of the Tear Film Lipid Layer," *Experimental Eye Research*, vol. 78, pp. 347-360, 2004.

Driver, Paul J. et al., "Meibomian Gland Dysfunction," *Survey of Ophthalmology*,vol. 40, No. 5, pp. 343-367, Mar.-Apr. 1996.

Gifford, Sanford R., "Meibomian Glands in Chronic Blepharo-Conjunctivitis," *Department of Ophthalmology, University of Nebraska Medical College*, Sioux Valley Eye and Ear Academy in Sioux City, pp. 489-494, Jan. 1921.

Goto, E et al., "Treatment of Non-Inflamed Obstructive Meibomian Gland Dysfunction by an Infrared Warm Compression Device," *Br J Ophthalmol*, vol. 86, pp. 1403-1407, Dec. 1, 2002.

Olson, Mary Catherine et al., "Increase in Tear Film Lipid Layer Thickness Following Treatment with Warm Compresses in Patients with Meibomian Gland Dysfunction," *Eye and Contact Lens*, vol. 29, No. 2, pp. 96-99, 2003.

Ong, Bee-Leng, "Clinical Diagnosis and Management of Meibomian Gland Dysfunction," *Contact Lens Spectrum*, Jun. 1, 1996.

U.S. Appl. No. 13/343,407, filed Jan. 4, 2012.

U.S. Appl. No. 13/645,985, filed Oct. 5, 2012.

U.S. Appl. No. 14/967,116, filed Dec. 11, 2015.

U.S. Appl. No. 15/364,070, filed Nov. 29, 2016.

U.S. Appl. No. 15/369,176, filed Dec. 5, 2016.

U.S. Appl. No. 15/374,426, filed Dec. 9, 2016.

U.S. Appl. No. 15/442,003, filed Feb. 24, 2017.

U.S. Appl. No. 15/639,850, filed Jun. 30, 2017.

U.S. Appl. No. 16/059,281, filed Aug. 9, 2018.

U.S. Appl. No. 16/127,870, filed Sep. 11, 2018.

Leahy-Smith America Invents Act, H.R.1249, 112th Cong. (2011), https://www.congress.gov/bill/112th-congress/house-bill/1249 H.R. 1249—112th Congress (2011-2012).

Lee, Jeanette, OD shares drug-free approach to treating meibomian gland dysfunction, https://www.healio.com/news/optometry/20120225/od-shares-drug-free-approach-to-treating-meibomian-gland-dysfunction, published: Nov. 1, 2009.

ZDNET, Why you need an Android smartphone with a thermal and IR camera. Jun. 22, 2022. Retrieved from the Internet May 7, 2025. [https://www.zdnet.com/article/why-you-need-anandroid-smartphone-with-a-thermal-and-ir-camera/].

* cited by examiner

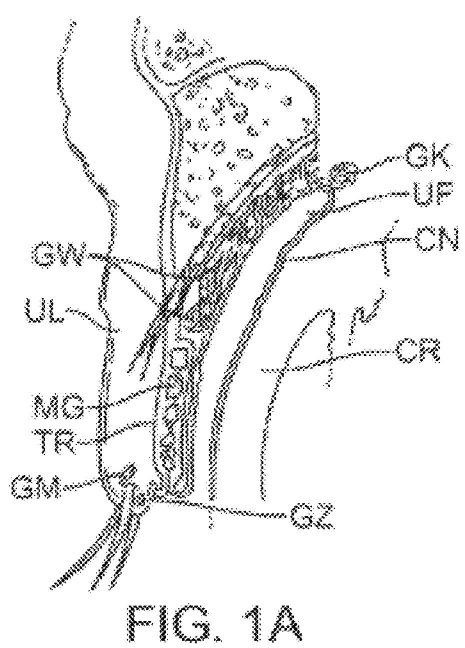
FIG. 1A
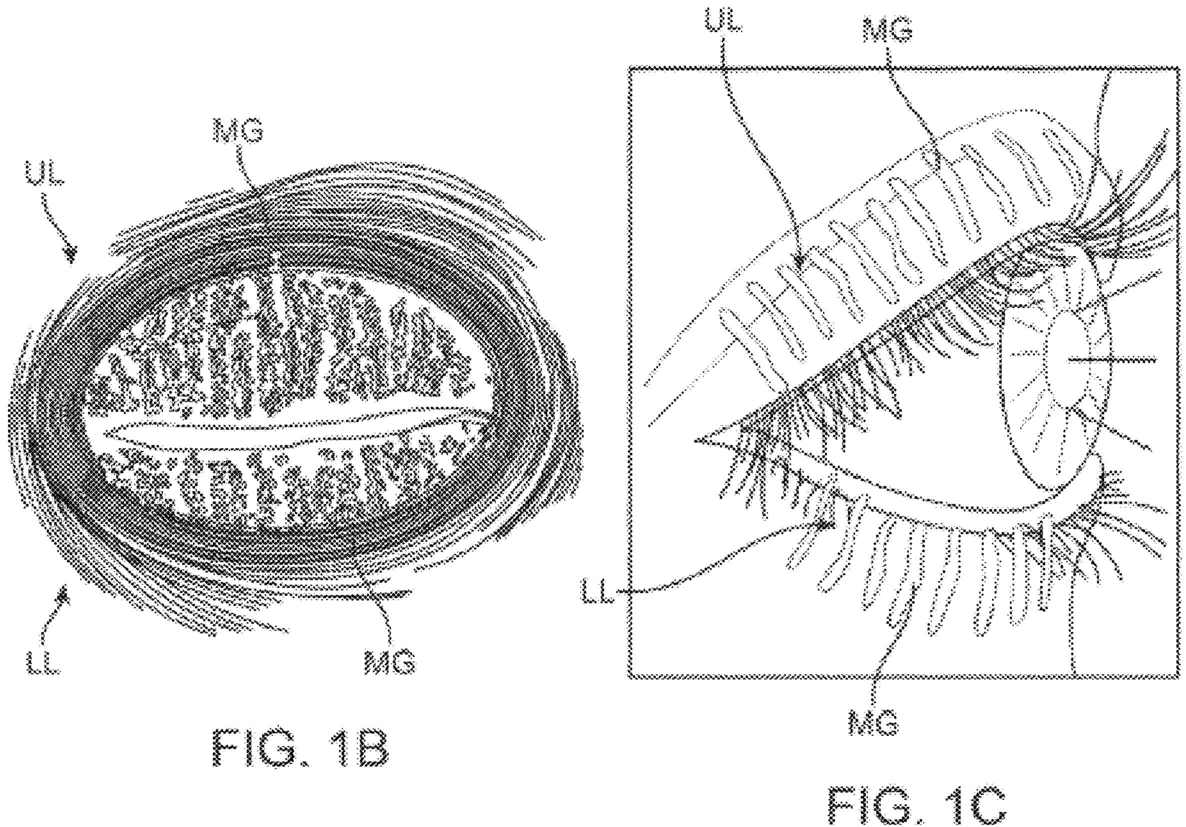
FIG. 1B
FIG. 1C

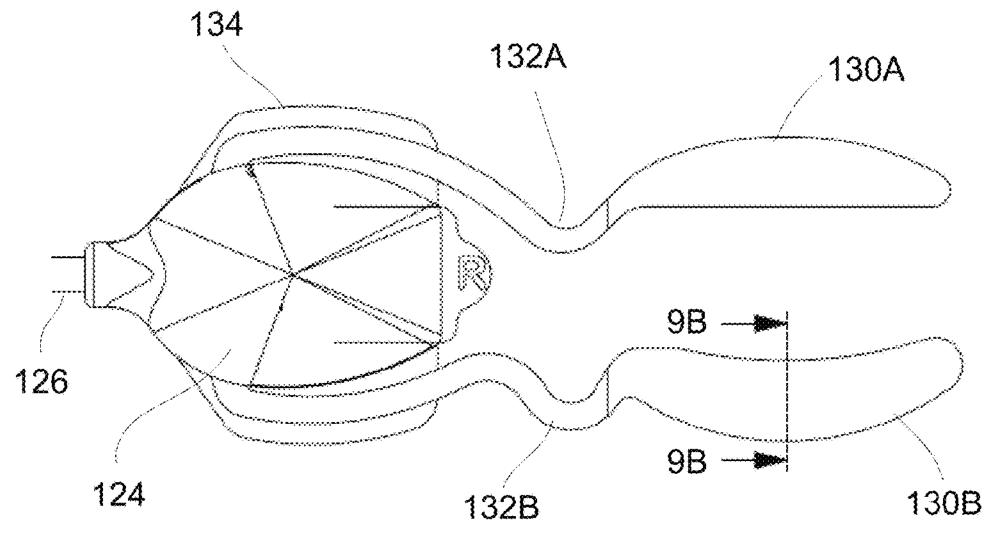
FIG. 9A
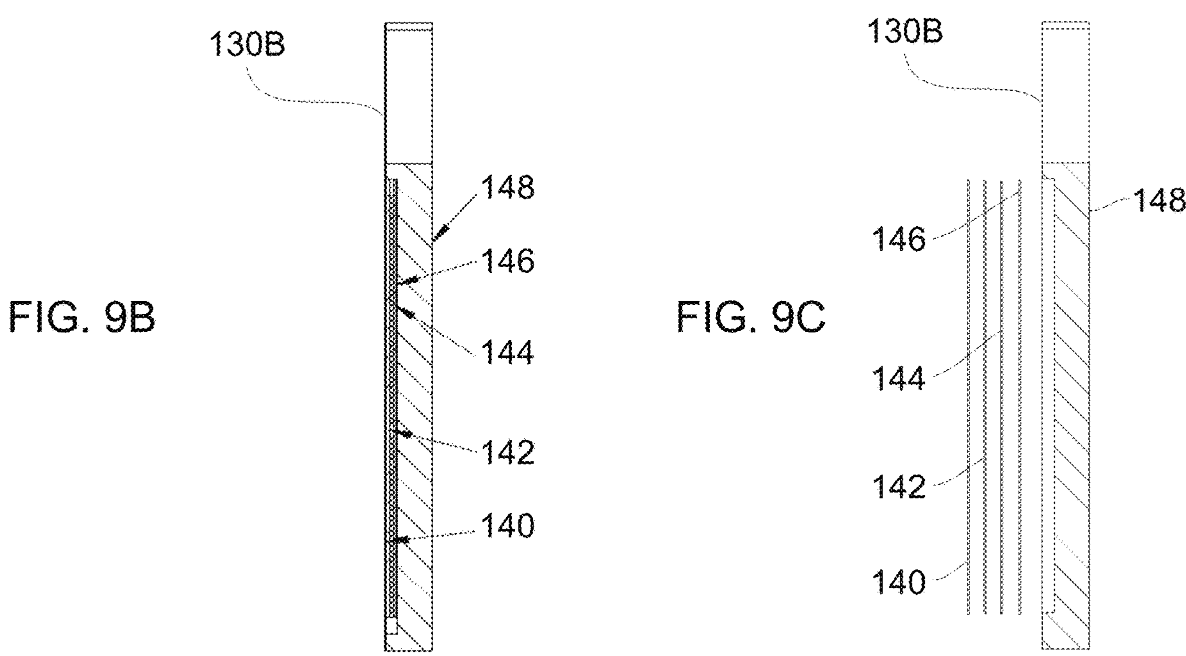
FIG. 9B
FIG. 9C

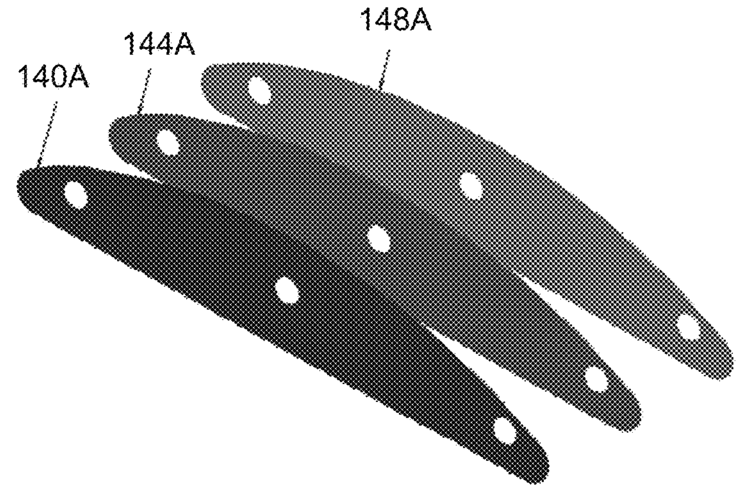
FIG. 11A
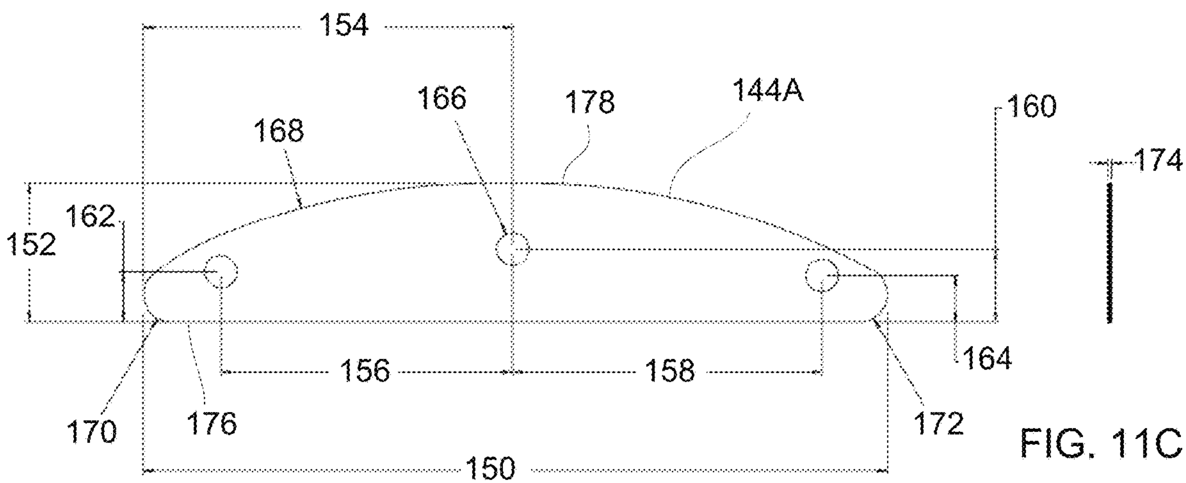
FIG. 11C
FIG. 11B

TREATMENT APPARATUS AND METHODS

FIELD OF THE INVENTION

The present invention relates to methods and apparatus for treatment of dry eye syndrome and other related conditions. More particularly, the present invention relates to methods and apparatus for the treatment of various eye-related conditions such as dry eye syndrome using adhesive strips which are specifically contoured or shaped to adhere to selected regions around a patient's eyes or peri-orbital region.

BACKGROUND OF THE INVENTION

Tears are a complex mixture of water, lipids, mucus, proteins and electrolytes and this mixture helps to maintain a smooth, lubricious, and optically clear optical surface and also helps to protect the eyes from infection. The tear film has three basic layers: oil, water, and mucus and problems or disturbances in any of these layers can cause ocular surface problems including dry eye symptoms.

The outermost layer of the tear film is typically comprised of an oil layer containing fatty acids and lipids (meibum), which are produced primarily by sebaceous glands called the meibomian glands located along the eyelid margin. The oil layer smoothes the tear surface and retards evaporation of the aqueous or watery middle layer. However, if the meibomian glands fail to produce enough oil, produce suboptimal fatty acid mixtures, or if the glands become obstructed or clogged, the watery layer typically evaporates too quickly causing dry eyes. A blockage or inflammation of the meibomian glands can, among many things, lead to enlarged glands or infections, inspissated secretions, styes, chalazia, hordeolum, or preseptal cellulitis. Dry eyes are thus common in people whose meibomian glands are obstructed or functioning improperly. The aforementioned are some examples of meibomian gland dysfunction which is also sometimes referred to as evaporative dry eye.

The middle watery layer of tears is composed primarily of an aqueous solution, which is produced by the lacrimal glands and accessory glands (tear glands). The middle layer cleanses the eyes and washes away foreign particles or irritants, maintains a clear optical medium, and keeps the ocular surface moist. The innermost layer of the tear film is composed primarily of mucus, which helps to spread the tears evenly over the surface of the eyes. A lack of mucus in the tear film is also associated with dry eye syndrome.

As discussed above, the meibomian glands are oil-secreting glands located within both the upper and lower eyelids. There are approximately 30 to 40 glands along the upper eyelid and approximately 20 to 30 glands along the lower eyelid with the ducts for each of the glands opening along the inner edge of the free margin of the respective lids by minute foramina through which their secretion is released to prevent the lids adhering to each other or to the ocular surfaces. An example of the location of the meibomian glands is illustrated in the cross-sectional view of the upper eyelid UL shown in FIG. 1A which illustrates the relative positioning of a single meibomian gland MG. Other glands and anatomical features are illustrated for reference, e.g., the glands of Wolfring GW, tarsus TR, gland of Moll GM, gland of Zeis GZ, gland of Krause GK, upper fornix UF, conjunctiva CN and cornea CR of the eye which is partially covered by the upper eyelid UL. As illustrated, the meibomian gland MG is positioned along a length of the upper eyelid UL (and lower eyelid LL) with the duct opening along the inner edge of the eyelid UL in proximity to a surface of the underlying eye.

FIG. 1B illustrates a front view of a patient's eye having the upper eyelid UL and lower eyelid LL in a closed position, such as when the patient blinks. As shown, the meibomian glands MG may be seen aligned adjacent to one another over both the upper UL and lower eyelids LL. FIG. 1C also shows a perspective view of a patient's eye in the open position to illustrate how the meibomian glands are typically aligned relative to one another when the patient's eye is opened.

Blinking is thought to be the primary mechanism to open the orifice of the meibomian glands and to generate compressive force to allow for the release of oily secretions from the glands. The natural blinking motion and blinking force causes the upper lid to pull or drag a sheet of the lipids secreted by the meibomian glands over the two underlying layers of the tear film thus forming the protective coating which limits the rate at which the underlying layers evaporate. It is estimated that at least 65% of meibomian gland disease or dry eye results from a defective lipid layer or an insufficient quantity of such lipids that results in accelerated evaporation of the aqueous layer. Hence, eyelid closure or blinking disorders, or other disorders that affect proper tear distribution, may also cause or exacerbate meibomian gland dysfunction or dry eye.

As the eyelids close in a total blink, the superior and inferior fornices, which hold a reservoir of tears, are compressed by the force of the preseptal muscles and the eyelids move toward one another. The upper eyelid, for instance, moves over the eye while exerting upon the eye surface a force which helps to clear the front of the eye of debris, insoluble mucin, and also expresses the oil secretions from the meibomian glands. The lower lid moves horizontally in the nasal direction and pushes debris toward both punctae, the openings that ultimately drain into the nasal cavities.

As the eyelids open the tear film is redistributed where the upper lid pulls the aqueous phase via capillary action and the lipid layer spreads as quickly as the eyelids move. Hence, eyelid movement is accordingly important in tear-film renewal, distribution, turnover, and drainage.

For a variety of reasons, the meibomian glands can become blocked, plugged, inflamed, or occluded resulting in meibomian gland dysfunction and dry eye disease. The obstruction that triggers the disease can occur anywhere within the meibomian gland, for instance, at the gland's surface or orifice preventing normal lipid secretions from flowing; in the main channel of the gland which may be narrowed or blocked; or in other locations deeper within the gland that lead to the main channel.

Treatments for blocked meibomian glands may include a number of conventional treatments. One course of treatment includes the application of soap and cleaning agents, eyelid scrubs, antiseptics, or antibiotics to reduce eyelid inflammation. Antibiotics such as tetracycline, doxycycline, minocycline, metronidazole, azithromycin, bacitracin, or erythromycin can be administered orally or topically to help regulate or improve meibomian gland lipid production. Inflammation on the surface of the eye may also be controlled with topical drugs such as corticosteroids or cyclosporine (RESTASIS®, Allergan, Inc., CA), or other anti-inflammatory compounds or immune-suppressants. Evidence suggests that ocular surface inflammation is not only associated with meibomian gland dysfunction but also with dry eye syndrome.

Other examples of dry eye treatments may include the application of prescription eye inserts for people with moderate to severe dry eyes symptoms who are unable to use artificial tears. An eye insert, e.g., hydroxypropyl cellulose (LACRISERT®, Merck & Co., Inc., NJ), may be inserted between the lower eyelid and eye. The insert dissolves slowly to release a substance which lubricates the eye. Alternatively, special contact lenses or amniotic membrane transplants may be used to shield the surface of the eye to trap moisture.

In other treatments, the patient's tear ducts may be closed to prevent the tear film from draining away from the surface of the eye too quickly by procedures such as insertion of punctal plugs into the tear ducts or cauterizing the tissues of the drainage area. Aside from implants or cauterizing treatments, dry eye syndrome may be treated using pharmaceutical agents such as eyedrops, ointments which coat the eyes, etc. Artificial tears, gels, ointments, autologous serum tears, or albumin drops have all been employed in the treatment of dry eye.

Additionally, warm compresses are also typically placed over the eyes and are used to restore function to the meibomian glands by melting any lipid plugs as well as incorporating massaging of the lids which may further reduce meibomian gland obstruction and express meibomian gland contents. However, application of warm compresses often can require their application two to three times daily during which time patients may incorrectly target only one of the affected lids and are also prevented from seeing out of the treated eye because of the compresses. Warm compresses pose multiple issues such as noncompliance, poor persistence, or high variability. Compresses may be too hot, further exacerbating inflammation, or they may cool too quickly preventing adequate therapeutic effect.

Other treatment devices have also been developed which cover the entire affected eye to apply heat and a massaging force directly to the affected eyelids. However, such devices, like the compresses, require that the patient's eyes be temporarily but completely obstructed during the treatment resulting in discomfort, lost productivity, and potentially lower compliance among patients. Additionally, these treatments require visits to a physician or healthcare provider, and thus are labor intensive, inconvenient, expensive, and consequently are not as well-suited for widespread consumer adoption.

There are also forceps that are used for expressing meibomian glands but these forceps are not customized or optimized for meibomain gland expression. Expression of the meibomian glands typically involves application of compressive force to the glands to express the secretions of the gland, also known as meibum, from the gland orifice. For instance, such forceps are neither heated nor dimensionally customized for directional expression of meibum.

Accordingly, there exists a need for methods and apparatus which are relatively simple to routinely use for the patient or physician to use and which also allow for the patient to continue their normal activities, is non-obtrusive and non-disruptive, and which also take advantage of the patient's natural physiological activities to facilitate treatment and which facilitates meibomian gland expression.

SUMMARY OF THE INVENTION

In treating conditions such as meibomian gland dysfunction (MGD), which is commonly associated with the evaporative form of dry eye syndrome (DES), the meibomian glands may be mechanically pressed or squeezed to express solidified meibum from the glands in order to help treat MGD. Forceps are typically used to apply pressure upon the meibomian glands in combination with a heat treatment. The forceps may also be used to debride the tissue along the upper and/or lower eyelid margins to facilitate the clearing of any internal or external obstructions, keratinization, or "capping" at or near the orifices or openings of the meibomian glands. The methods of treatment described may also be used for other procedures as well, e.g., improved vision, contact lens comfort improvement, tear quality improvement, surgical outcome improvement due to accurate measurements from an improved tear quality or optical surface, etc.

With respect to the assembly for the treatment strip or strips, the assembly may generally comprise one or more strips configured to adhere to an underlying region of skin in proximity to one or both eyes of a subject such that the one or more strips allow for the subject to blink naturally without restriction from the one or more patches. Moreover, the one or more strips may be configured to emit energy or therapy to the underlying region of skin and where the one or more strips are shaped to follow a location of one or more meibomian glands contained within the underlying region of skin.

A programmable controller having a controller board and a processor may be in communication with the one or more strips, where the controller may induce, and monitor a programmable temperature of the one or more heater strips and to provide a treatment therapy. The therapy may be programmed to maintain a set point, within a known accuracy, (e.g., 42° C.+/−1° C.) above a threshold temperature of, e.g., 39° C., and below a maximum temperature of, e.g., 48° C., over a treatment period of, e.g., 15 minutes. Other treatment times may be implemented in other variations; for instance, the treatment time may extend from 1 minute to 60 minutes in other treatment variations.

In use, the one or more strips may be adhered to a region of skin in proximity to one or both eyes of a subject such that the one or more strips allow for the subject to blink naturally without restriction from the one or more patches. While adhered, the strips may treat or emit energy to the region of skin, where the one or more strips are shaped to follow a location of one or more meibomian glands contained within the region of skin. Alternatively, while the strip may not directly overly a meibomian or other ocular or orbital gland, it may deliver energy or absorb energy from underlying neighboring tissue or vasculature, which ultimately diffuses, or supplies said glands, respectively. In other words, heating or cooling the blood supply to the eyelids, meibomian glands, and/or lacrimal glands using these strips may affect their function and metabolism while not necessarily needing to directly overlay them in particular variations. For instance, the strips may effect the heating or cooling via any heat transfer modality, e.g., radiation, conduction, convection, or any combination thereof, without directly overlaying upon the tissue.

The upper strip may thus have an upper curved or arcuate periphery which is shaped to extend and follow the upper (or superior) border of the meibomian glands (such as along or up to the upper eyelid crease) while the straightened periphery of the lower edge may be shaped to extend and follow the lower (or inferior) border of the meibomian glands such as along the free margin of the upper eyelid. Although straightened, the lower edge may be gently curved or arcuate in alternative variations. The lower strip may similarly have an upper straightened periphery to extend and follow the upper (or superior) border of the meibomian glands along the free margin of the lower eyelid and a lower curved or arcuate periphery to extend and follow the lower (or inferior) border of the meibomian glands along the lower eyelid (such as along or up to the lower eyelid crease). Alternatively, the upper periphery of the lower strip may also be gently curved or arcuate in alternative variations as well.

In other words, with the tarsal plate containing the meibomian glands, which span from proximal to distal, the peripheral edges of the treatment strips may correspond to the distal eyelid margin and proximal peripheral edge and the treatment strips can assume multiple configurations. Generally, the peripheral distal edge of the treatment strip may be relatively straight or assume a gentle curve either of which can follow the underlying distal eyelid margin and tarsal plate while having a proximal peripheral edge that is relatively curved to assume the more curved proximal edge of the underlying tarsal plate.

The strips may be used individually for placement upon only the upper eyelid or only the lower eyelid depending upon the desired treatment. Moreover, the lengths of the treatment strips may also be varied to target individual meibomian glands for providing a targeted treatment, if desired, and as described in further detail herein. Additionally, while the treatment strips may be sized generally, they may also be custom made or sized for a specific individual's eyelid dimensions.

Because of the specific contoured sizes and flexibility of the treatment strips the treatment strips may be placed upon the patient to apply therapy to the underlying meibomian glands allowing the patient's eyes to be opened and closed normally without interference from one or both treatment strips. Accordingly, the treatment strips contoured size, shape, thickness, and flexibility allow for treatment to occur while also allowing for the patient to have one or both eyes remain opened such that normal, physiologic blinking can proceed during the course of treatment. To further reduce the forces on the eyelids, heaters may be decoupled from the forces acting on their connections (such as wires) by the addition of multiple turns (e.g., non-linear regions) in their connection paths that destabilize loads that would otherwise be communicated from power supply cabling to the eyelid (s). Rather than relying on an application of any type of external force, the treatment strips take advantage of the eye's natural mechanism for clearing oil from the meibomian glands via blinking. Hence, the treatment strips may be adhered in place for treatment without any further intervention by the patient or healthcare provider such that the treatment strips may apply, e.g., heat energy, to melt or liquefy any waxy or solid meibomian gland obstructions while the eyes remain unobstructed and are allowed to blink naturally. The treatment strips thus allow for the natural blinking force to clear the glands of the heat-treated softened obstructions before they have re-solidified unlike other treatments which require that the patient keep their eyes closed or obstructed during the course of a treatment and prevent or inhibit the patient from blinking.

In another variation of the treatment strip assembly, each of the heating strips may have several different layers incorporated. A substrate such as a flexible printed circuit board assembly (FPCBA) having one or more heating elements (e.g., resistive heating elements) may be incorporated throughout the FPCBA layer and positioned to contact the skin surface of the eyelid under treatment. An adhesive layer may attach the FPCBA layer to a ductile layer which may serve different functions. The ductile layer may be configured to conform to the anatomy of the underlying tissue surface upon which the heating strip is adhered to enable the strip to conform closely to the tissue surface. Once the ductile layer has conformed, it may retain its shape through the course of the treatment to facilitate conductive heat transfer to the tissue and also to increase comfort to the user. Furthermore, the ductile layer may conduct the heat emitted from the FPCBA layer evenly over the entire heating strip assembly to facilitate the treatment of the underlying tissue surface. Hence, to provide the flexibility and structural support to retain a conformed shape as well as to provide efficient heat conduction throughout the heating strip, the ductile layer may be fabricated from, e.g., a metallic material or metallic alloy material, e.g., copper, aluminum, nickel, gold, etc. The thickness of the ductile layer may also be varied depending upon the material used as properties such as conductivity and yield strength will vary between the various material types utilized.

An additional insulating layer (e.g., electrically insulating layer) may be provided adjacent to the ductile layer and an outermost layer, e.g., foam layer, which may be the outermost layer away from the underlying skin surface and which may be provided to ensure that the heat generated by the underlying substrate layer is retained or directed inwardly toward the eyelid skin and tissue rather than being dissipated into the environment. Each of the layers provided may be assembled such that the heating strip presents a flush and smooth surface without any projections which may injure or irritate the contacted tissue skin surface.

The heating strips may be dimensioned differently depending upon the anatomy of the patient or other factors. For instance, the strips may be configured into multiple sizes for different patient types (e.g., pediatric, adult, male, female, etc.) and/or the strips may be dimensioned into different standardized sizes (e.g., small, medium, large, etc.) for each particular patient type, if so desired. Alternatively, different sized heating strips may be utilized between a first and second heating strip assembly used for a single patient depending upon anatomical differences. Moreover, each of the layers and the heating strip assemblies may be similarly or identically dimensioned for placement upon the upper eyelid.

In one variation of the heating strip system, the system may generally comprise a substrate layer having one or more heating elements incorporated, a ductile layer attached in proximity to the substrate layer and configured to conform and retain a shape of the heating strip to an anatomy of an underlying region of skin of an eyelid of a subject, and a protective layer attached in proximity to the ductile layer, wherein the heating strip is configured to adhere to the underlying region of skin and where the heating strip has a flexibility sufficient to accommodate movement of the eyelid to allow for the subject to blink naturally without restriction from the strip. The system may further include a controller which is programmable for a treatment therapy and which is in communication with the substrate layer via a connecting cable which transmits electrical energy to the substrate layer which receives the electrical energy and emits thermal energy which is conducted throughout the strip via the ductile layer to the underlying region of skin.

In one variation of a method of treating a subject, the method may generally comprise conforming a heating strip to an underlying region of skin of an eyelid of a subject via a ductile layer within the heating strip such that the heating strip retains a shape of an anatomy of the underlying region of skin, initiating a treatment with the heating strip via a controller transmitting electrical energy to a substrate layer of the heating strip having one or more heating elements via a connecting cable, wherein the substrate layer is attached in proximity to the ductile layer, and conducting thermal energy from the substrate layer throughout the heating strip via the ductile layer and into the underlying region of skin.

Furthermore, any of the forceps variations and combinations described herein may be used alone for treating a patient or they may be used in combination with any of the treatment apparatus and methods described in further detail in U.S. Pat. Nos. 9,724,230; 9,510,972; 9,844,459; 9,642,743; 10,052,226, and U.S. Pat. Pubs. 2016/0106576; 2017/0304110; 2017/0087009; 2018/0344512; and U.S. patent application Ser. No. 16/127,870 filed Sep. 11, 2018, each of which is incorporated herein by reference in its entirety and for any purpose herein, particularly for treatment of MGD and dry eye syndrome.

BRIEF DESCRIPTION OF THE DRAWINGS

FIG. 1A shows a cross-sectional side view of an upper eyelid and an example of the location of a meibomian gland.

FIG. 1B shows a front view diagram of meibomian gland distribution in human eyelids having the upper eyelid and lower eyelid in a closed position, such as when the patient blinks, and the alignment of the meibomian glands over both the upper and lower eyelids.

FIG. 1C shows a perspective view of a patient's eye in the open position to illustrate how the meibomian glands are typically aligned relative to one another when the patient's eye is opened.

FIG. 9A shows a top view of a treatment strip assembly configured for application to the upper and lower eyelids of a user's eye, e.g., right eye.

FIGS. 9B and 9C show cross-sectional and assembly side views of a treatment strip assembly illustrating the various layers.

FIG. 11A shows a perspective assembly view of some of the layers of the treatment strip assembly configured for an upper eyelid.

FIGS. 11B and 11C show top and side views of the metallic layer configured for an upper eyelid.

FIGS. 12B and 12C show top and side views of the metallic layer configured for a lower eyelid.

DETAILED DESCRIPTION OF THE INVENTION

Figure 2A:
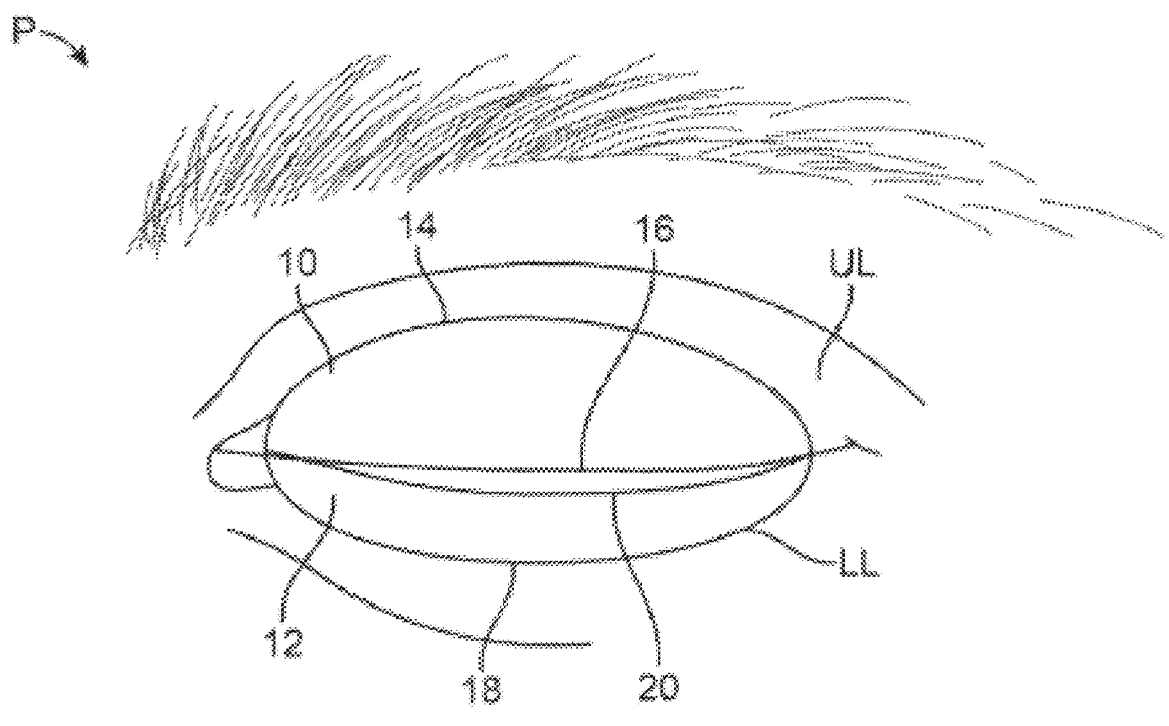
FIG. 2A shows a front view of a patient's eye in a closed position with an example of treatment strips which adhere onto the upper or lower eyelids (or both) and where the strips are sized or contoured for placement directly over the meibomian glands located in the underlying eyelids.

In treating conditions such as meibomian gland dysfunction (MGD), which is commonly associated with the evaporative form of dry eye syndrome (DES), the meibomian glands may be mechanically pressed or squeezed to express solidified meibum from the glands in order to help treat MGD. Forceps are typically used to apply pressure upon the meibomian glands. The forceps may be modified to create a pressure gradient upon the meibomian glands to direct meibum and any other meibomian gland secretions towards the meibomian gland orifices. The forceps may be configured to further provide for debridement of the tissue along the upper and/or lower lids to facilitate the clearing of any obstructions such as inspissated oil and meibum plugs from the main ducts and orifice openings of the meibomian glands, meibomian gland channel, and meibomian gland orifices. Additionally and/or alternatively, the forceps may be configured to also provide a thermal treatment, e.g., to the eyelid surfaces to simultaneously melt, soften, or liquefy and express meibum to increase its therapeutic efficacy.

The forceps may be used before, during, and/or after a heat treatment in combination with the heating strips as described herein. Alternatively, the forceps may be used to first apply a heat treatment to melt the meibum plugs contained within the glands and then the forceps may be used to mechanically express the liquefied meibum before it re-solidifies. In another alternative, the forceps may be used to apply a thermal treatment and mechanical expression simultaneously to effectively express the meibum. In treating the meibomian glands, the forceps may also be used to apply heat to other regions, e.g., inner eyelids, outer eyelids, or both. However, when the heating strips are used to apply a heat treatment to a patient, the forceps used for mechanically expressing the glands may be configured to separately heat the glands and/or they may include any number of mechanical features, as described herein, to facilitate mechanical expression.

In treating conditions such as meibomian gland dysfunction (MGD), which is commonly associated with the evaporative form of dry eye syndrome (DES), a patch, strip or thin adhesive device can be affixed to the skin of the upper and/or lower eyelids to deliver or absorb heat or other forms of energy, pressure, drugs, moisture, etc. (alone or in combination) to the one or more meibomian glands contained within the underlying skin. In particular, the treatment strip or strips may be configured and sized specifically for placement over one or more targeted meibomian glands contained within the skin of the upper and/or lower eyelids. The application of thermal therapy, e.g., heating or cooling, can cross the eyelids quite easily as the eyelids are generally the thinnest skin found on the human body and the tissue is highly vascularized. With the root of the eyelid located proximally and the eyelid margin located distally, the net arterial flow of blood flows from proximal to distal. So wherever these treatment strips are placed, the heating or cooling therapy may easily be carried throughout the eyelid and any structures contained therein, e.g., meibomian glands MG, lacrimal glands LG, gland of Zeis GZ, gland of Moll GM, gland of Wolfring GW, gland of Kraus GK, etc.

Moreover, because the eyelid is so thin, the heating or cooling therapy can be transmitted to the ocular surface and the eye itself (described in further detail below). Thus, the therapy can impart energy to the conjunctiva, goblet cells, episcleral vasculature, cornea, aqueous humor, iris, ciliary body, and possibly the retina, choroid, optic nerve, anterior vitreous, and lens. Thus, any thermal therapy by the treatment strips may also impact and be used to treat ocular surface disorders and anterior segment diseases, e.g., conjunctivitis, keratitis, keratopathy, iritis, cyclitis, glaucoma, cataract, etc. Also, there may be use in the postoperative state-like after LASIK, PRK, or cataract or corneal surgery or other ocular, peri-ocular, intraocular, or eyelid surgery, as described in further detail below.

Figure 2B:
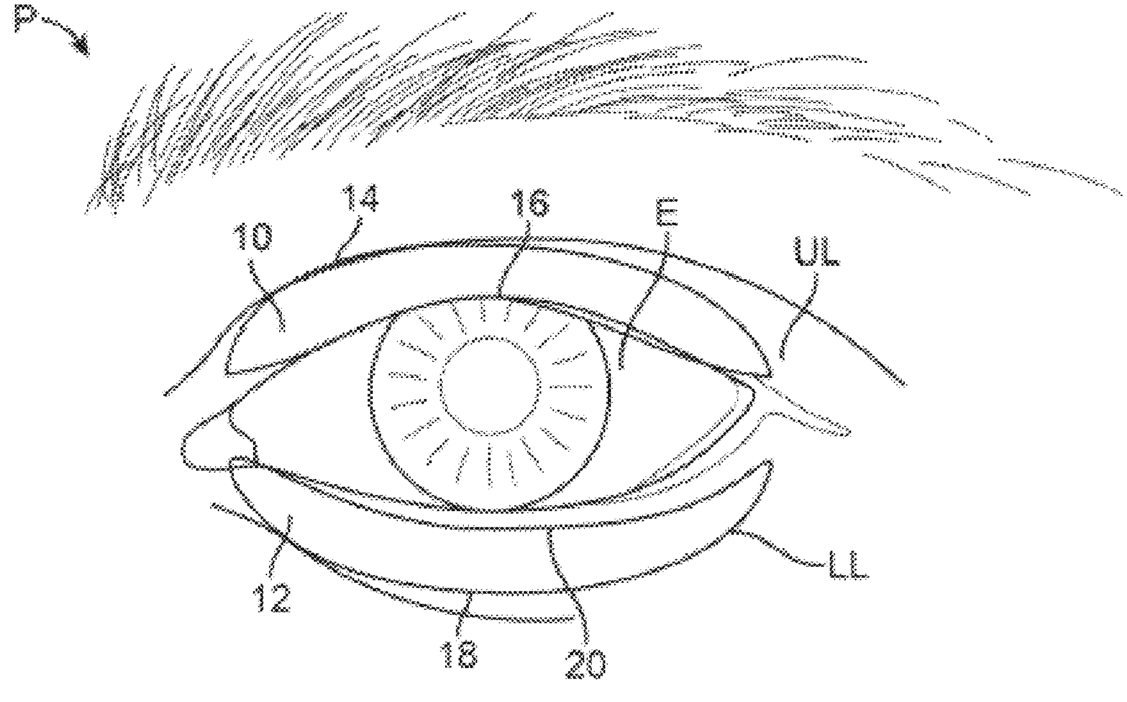
FIG. 2B shows the treatment strips of FIG. 2A illustrating how the strips may remain adhered to the patient skin while allowing for the eyelids to retract and allow for the patient to continue blinking while viewing normally out of the eye. While the strips may be applied from eyelid margin to eyelid crease, they may alternatively flex or accordion and/or compress during blinks to prevent impairment of normal blinking and maximize comfort.

As shown in the front view of FIG. 2A and FIG. 2B, one variation of such treatment strips may be seen as being adhered temporarily upon the upper eyelid UL and lower eyelid LL over an eye of a patient P when closed for illustrative purposes. The contoured upper strip 10 may be sized for adherence directly upon the skin of the upper eyelid UL such that the strip 10 has a configuration and shape which follows the location of the one or more meibomian glands contained within the underlying skin of the upper eyelid UL Likewise, the contoured lower strip 12 may also have a configuration and shape which follows the location of the one or more meibomian glands contained within the underlying skin of the lower eyelid LL. In other variations, the contoured strip may stop at the eyelid crease or cross over it as described in other variations below.

The upper strip 10 may thus have an upper curved or arcuate periphery 14 which is shaped to extend and follow the upper (or superior) border of the meibomian glands (such as along or up to the upper eyelid crease) while the straightened periphery 16 of the lower edge may be shaped to extend and follow the lower (or inferior) border of the meibomian glands such as along the free margin of the upper eyelid UL. The lower strip 12 may similarly have an upper straightened periphery 20 to extend and follow the upper (or superior) border of the meibomian glands along the free margin of the lower eyelid LL and a lower curved or arcuate periphery 18 to extend and follow the lower (or inferior) border of the meibomian glands along the lower eyelid LL (such as along or up to the lower eyelid crease). The use of the terms lower and upper herein refer to the periphery of the treatment strips when placed upon the patient P (human or animal) and are used herein for descriptive purposes.

While the treatment strips 10, 12 are both shown adhered upon the respective upper eyelid UL and lower eyelid LL, the strips 10, 12 may be used individually for placement upon only the upper eyelid UL or only the lower eyelid LL depending upon the desired treatment. Moreover, the lengths of the treatment strips 10, 12 may also be varied to target individual meibomian glands for providing a targeted treatment, if desired, and as described in further detail herein.

While the treatment strips 10, 12 are shown placed upon the closed eyelids of the patient P, the strips 10, 12 are arc-shaped or flexible enough to assume the curvature of the patient's eyelid margin and may be long enough to cover some or all of the underlying meibomian glands in the tarsal plate. While the treatment strips 10, 12 may be sized generally, they may also be custom made or sized for a specific individual's eyelid dimensions or shaped to optimize adhesion and/or comfort and/or stability. Generally, the treatment strips 10, 12 may have a length anywhere from about 1 mm to 50 mm depending upon the desired treatment length as well as the anatomical considerations of the patient since the typical palpebral fissure length in an adult is about 27 mm to 30 mm. Thus, to cover as many as all of the meibomian glands, the treatment strips 10, 12 may be sized to have length of, e.g., 25 mm to 30 mm, or if sized to cover just beyond all the meibomian glands, a length of, e.g., 30 mm to 50 mm (or more if needed to optimize coverage/adhesion/comfort/stability). Moreover, one or both treatment strips 10, 12 can have a width ranging anywhere from about 1 mm to 25 mm since the typical eyelid crease in a Caucasian male is about 8 mm to 9 mm above the eyelid margin while in Caucasian females it is about 9 mm to 11 mm above the eyelid margin (or more if needed for adhesion/comfort and potentially increased efficacy from heating or cooling the inbound blood flow). Customization enables it to fit any particular anatomy, race, ethnicity, etc. Moreover, the treatment strips may be manufactured with varying levels of flexibility to accommodate the ergonomics of the eyelid and eyelid blink for optimal comfort and minimal obtrusiveness or movement.

Because of the specific contoured sizes and flexibility of the treatment strips 10, 12, the treatment strips may be placed upon the patient P by the patient himself/herself for consumer use or by a healthcare provider to apply therapy to the underlying meibomian glands allowing the patient's eyes to be opened and closed normally, as shown in FIG. 2B, without interference from one or both treatment strips. While the strips may be applied from eyelid margin to eyelid crease, they may alternatively flex or accordion and/or compress during blinks to prevent impairment of normal blinking and maximize comfort.

Typical treatment patches, such as for application of a warm compress, are generally sized for placement over the entire eye or eyes such that the patient is unable to open their eyes or blink during a treatment session. Yet, because of the strong association between DES and MGD (for instance, MGD includes the spectrum of MGD, meibomitis, blepharitis, and ocular rosacea), natural blinking by an individual is the mechanism by which meibomian gland secretions are normally released onto the eyelid margin and over the tear. In the absence of blinking, the oil contained within the meibomian glands remain unexpressed within the glands' terminal ducts and fail to contribute to distribution of the oily layer upon the tears.

Accordingly, the treatment strips 10, 12 contoured size, shape, and flexibility allow for treatment to occur while also allowing for the patient to have one or both eyes remain opened such that normal, physiologic blinking can proceed during the course of treatment. Rather than relying on an application of any type of external force to express the oil or obstruction from the glands, the treatment strips 10, 12 take advantage of the eye's natural mechanism for clearing oil from the meibomian glands via blinking. Hence, the treatment strips 10, 12 may be adhered in place for treatment without any further intervention by the patient or healthcare provider such that the treatment strips 10, 12 may apply, e.g., heat energy, to melt or liquefy any waxy or solid meibomian gland obstructions while the eyes remain unobstructed and are allowed to blink naturally. The treatment strips 10, 12 thus allow for the natural blinking to help clear the glands of the heat-treated softened obstructions before they have re-solidified unlike other treatments which require that the patient keep their eyes closed or obstructed during the course of a treatment and prevent or inhibit the patient from blinking. Delivery of heat may also increase blood flow by promoting vasodilation as increased delivery of blood can affect metabolism, temperature of other tissues, may have effects on inflammation, and can thereby improve tissue function or recovery.

Because some patients have obstructions or occlusions in their meibomian glands that may not sufficiently melt, loosen, or soften without attaining heightened temperatures at the meibomian glands, the treatment strips 10, 12 may apply heat or other treatments to the surface of the eyelids for a significant period of time for relatively longer treatment times and at higher treatment temperatures because of the ability of the treatment strips 10, 12 to remain attached to the patient during any given period throughout the day. Treatment strips may be relatively transparent or skin toned, and thereby inconspicuous, to allow for normal functioning throughout the treatment ranges. Patients can assume their daily activities with their eyes open and eyes blinking and with the comfort of a strip-based treatment. Moreover, patients can affix the treatment strips as many times as needed throughout the day, week, month, etc. until dry eye symptoms subside. This increases the frequency of treatment, convenience of treatment, and thus efficacy of treatment.

Because of the prolonged treatment times, the application of a separate force beyond the application of the strips may not be needed so long as the patient is able to continue blinking during the course of treatment. Moreover, the treatment frequency may be adjusted or varied depending upon the severity of the condition to be treated. One example for potential treatment frequency may include application of one or both strips, e.g., up to six times per day for ten minutes or up to an hour or more for each treatment. Moreover, because the treatment strips are positioned over the meibomian glands which overlie the ocular surfaces, the application of the heating therapy may also indirectly heat the ocular surface as well and may further reduce any chronic ocular surface inflammation, chronic conjunctival inflammation, or corneal neovascularization.

Aside from heating of the ocular surface, heat therapy may also optionally be used to potentially provide for indirect heating through the ocular surface as well for heating of the retina to provide a thermal therapy to limit inflammation and neovascularization which are underlying conditions for diseases such as age-related macular degeneration (AMD), retinal vascular occlusions, retinal neovascularization, glaucoma, retinal degenerations and dystrophies, and Diabetic Retinopathy.

While the treatment strips 10, 12 may be used throughout the day to take advantage of the patient's physiologic blinking, the treatment strips 10, 12 may also be used while the patient is resting or sleeping or while the patient simply maintains their eyes closed. The treatment strips 10, 12 may be applied as a single-use treatment or they may be configured to be robust enough as a re-usable device. In a re-usable embodiment, the adhesive component might be easily replaced while the thermal mechanism, circuitry, and sensors of the treatment strips are re-used.

The treatment strips 10, 12 are desirably flexible enough to accommodate movement of the upper eyelid UL and/or lower eyelid LL which may move as much as about 15 mm or more. Thus, the treatment strips 10, 12 may be fabricated from various materials.

Figure 3:
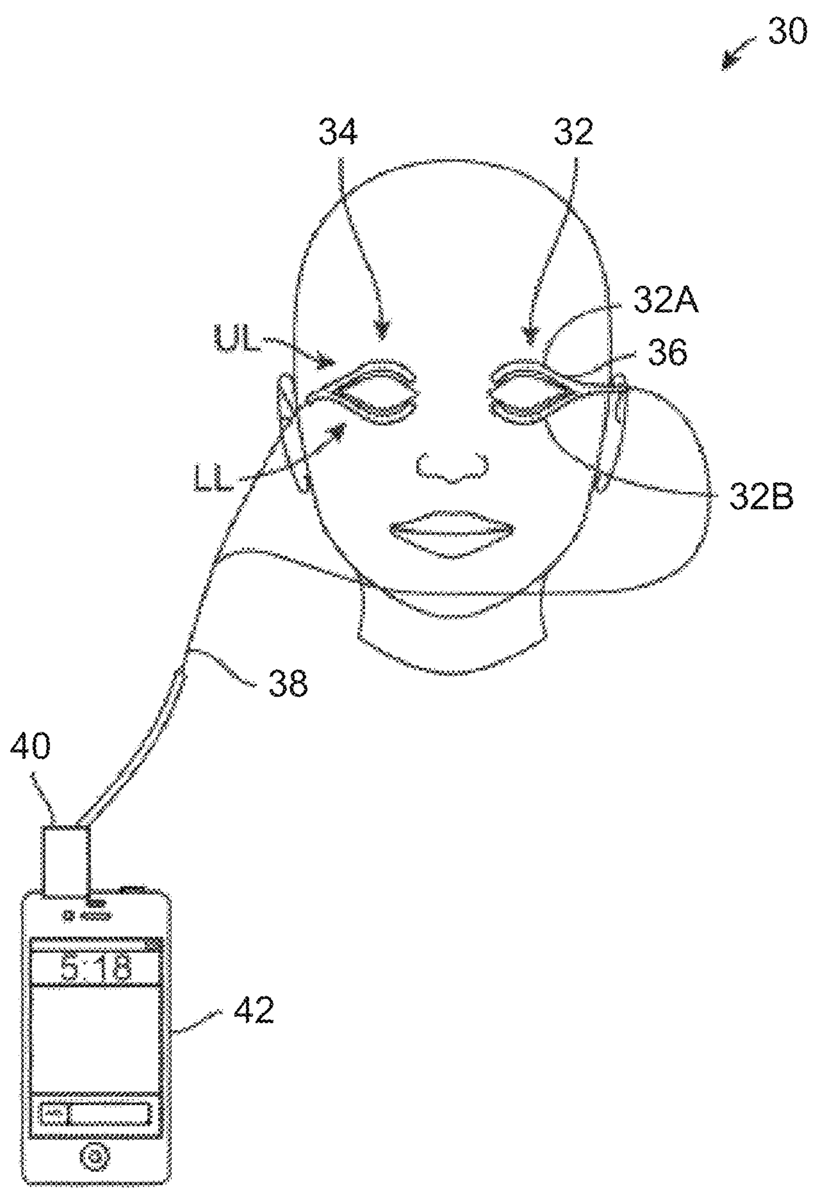
FIG. 3 shows yet another variation of an eyelid treatment system which may be coupled to a portable remote controller such as a smartphone or tablet.

FIG. 3 shows another variation where the eyelid treatment system 30 may be formed into a coupled dual-strip design, e.g., a "wishbone" design, where the dual-strip heating strips may have two heating elements which follow the location of the meibomian glands the upper UL and lower LL eyelid of a single eye. Depending upon whether both eyes or a single eye and/or both upper and lower eyelids are treated, the system 30 may comprise a first heating strip assembly 32 and a second heating strip assembly 34 for each respective eye. Each of the assemblies 32, 34 may accordingly utilize an upper and a lower lid treatment heater, e.g., upper lid treatment strip 32A and lower lid treatment strip 32B, where each of the upper and lower elements may be coupled to one another via wires 36 (e.g., flexible circuit). Moreover, each of the assemblies 32, 34 may be coupled via a connecting cable 38 to controller 40 which may be coupled (e.g., through an input/output port such as a headphone jack, USB port, micro HDMI, or other connection port) to a portable electronic device 42 (e.g., smartphone having a touch screen interface, tablet, PDA, laptop computer, etc.) as shown.

In other variations, the number of connecting cables may range anywhere from 1-4 connector cables rather than utilizing a single cable 38. For instance, one cable may be used to provide power and communication to a few or all four heating elements in each of the assemblies 32, 34. Alternatively, four connecting cables may provide power and communication to each of the heating elements in assemblies 32, 34. Yet in other alternatives, two connecting cables may provide power and communication to each of the assemblies 32, 34.

In other additional variations, any of the treatment strips described may be used in combination with the controller 42 described herein, as practicable. Yet in a further variation, oval or circular shaped heating elements may cover the eye and both eyelids where an outer border of the heating elements or strips may follow the path of the upper and lower meibomian glands. In this case, one treatment strip may cover both eyelids and both sets of meibomian glands and the user may use a total of two (rather than four) round, circular, or oval shaped treatment strips to cover both eyes. Such a variation may be used, e.g., for a night time therapy in bed prior to or during sleep when the eyes need not necessarily be open.

The assemblies 32, 34 may generally comprise strips, as previously described, which follow the location of the meibomian glands while still allowing patients to blink easily and proceed in comfort with daily activity. An example of such heaters which may be configured for use with the treatment system 30 may include thin, flexible heaters which are commercially available through companies such as Minco Products, Inc. (Minneapolis, Minn.) or can be custom designed and manufactured independently or through third party manufacturing. Each individual treatment strip, e.g., treatment strips 32A, 32B, may each be sized for a single eyelid, e.g., 28 mm×7 mm×0.15 mm, having a bottom chord length of, e.g., 28 mm, with a radius of curvature of, e.g., 75 mm, and having a general configuration of an arcuate rectangle having blunted corners where the nasal or temporal edges may coincide with the radii of the arc. However, these size limitations are intended to be exemplary and not limiting since the treatment strips 32A, 32B may be sized to be smaller or larger to accommodate different eye anatomies.

Moreover, the individual treatment strips 32A, 32B may be formed as thin, flexible transparent polymers containing the heating elements while the contact surface of the strips may be affixed to the respective eyelids with, e.g., a disposable adhesive. Other variations may utilize opaque or colored strips, e.g., skin-tone colors. Moreover, one or more temperature sensors may also be integrated into the treatment strips where the heating elements and sensors may be routed through the connecting cable 38 to a power source and/or controller 40 and/or portable electronic device 42, as shown.

Controller 40 may generally comprise a hardware/software platform or unit which may be programmed for controlling the therapy treatments. Accordingly, the controller 40 may include a processor as well as a power supply such as a battery (rechargeable or disposable) for providing power to the assemblies 32, 34. The power supply within controller 40 may be optionally rechargeable separate from the portable electronic device 42 or the power supply may draw power for the assemblies 32, 34 and processor directly from the portable electronic device 42 as well.

In the case where the controller 40 is programmed to provide the therapy treatment protocols, one or several controls for controlling the treatments may be built directly into controller 40. The portable electronic device 42 may interface with the controller 40 to display, in one variation, part of the controls on a screen (e.g., touchscreen) of the electronic device 42 such as controls for starting and/or stopping a treatment. The controller may also have facilities for detecting when leads are not properly connected, measuring power levels, and measuring temperature levels. Accordingly, there will be the capability to notify or alert a user should any of these values fall out of range or the ability to prevent initiation of treatment or cease treatment until these scenarios are explicitly acknowledged or corrected. Alternatively, all of the controls may reside on the controller 40 while a display on the electronic device 42 may serve primarily to show or track various results or treatment parameters, and or treatment status. A separate display and controller combination may also be used.

In yet another alternative, the all of the controls may reside on the display of the electronic device 42 for controlling the various treatment options and parameters rather than on the controller 40. In this variation, the electronic device 42, in this example a smartphone, may also provide the power to the treatment strip assemblies 32, 34 and may also control the various treatment temperatures and times as well as receive and display temperature feedback or other physiological parameters which may be measured. In this case, the treatment strips 32, 34 and connecting cable 38 may be plugged directly into the mobile or portable consumer electronic device 42. For instance, the electronic device 42 may be used to display treatment parameters and controls such as an icon or button for initiating therapy. In one example, therapy may be initiated by the user through electronic device 42 to heat one or more of the strips of one or both of the treatment strip assemblies 32, 34. In any of the variations, the electronic device 42, particularly in the case of a smartphone or tablet, may have an optional program or application downloaded onto the device which facilitates the various control and/or display parameters on the electronic device 42 depending upon how the electronic device 42 is used with the controller 40 and assemblies 32, 34. Depending on the variation, the display and control display may reside on the controller 40 itself or on another device separate from the controller 40.

Additionally, the electronic device 42 may also provide a diagnostic function to allow the user to test for dry eye and/or to determine how treatment is progressing either before, during, or after treatment. Accordingly, the electronic device 42 or controller 40 may leverage, e.g., an integrated camera and/or flash/light source, for purposes of imaging the user's ocular tear film or ocular surface and evaluating commonly used tear assessment criteria such as total tear film layer thickness, and/or tear film mucin layer thickness, and/or tear film lipid layer thickness, and/or tear film aqueous layer thickness, or any combination thereof. Such a camera may also display or "mirror" strip placement for evaluation or adjustment by the user or remotely, either synchronously or asynchronously. In addition to imaging of the user's tear film and/or ocular surface conditions, the mobile application may include other common methods for diagnosing dry eye such as user questionnaires related to the user patient's symptoms, discomfort, and/or improvement or worsening of symptoms that can be completed using the electronic device's touch screen interface, results stored on the electronic device 42 or web application or manufacturer's servers, tracked over time for trend evaluation, and possibly shared with the user's physician.

Moreover, in any of the variations, the controller 40 and/or electronic device 42 may be programmed or initiated to heat up the assemblies 32, 34 to, e.g., 42.5° C.+/−1° to 2° C. Treatment time may be set to, e.g., 1 to 30 minutes or more such as 60 minutes, and the controller 40 and/or electronic device 42 may further be programmed to shut down when the allotted treatment time has passed or if the measured temperature rises above a predetermined level, e.g., 45° C. Additionally, the controller 40 and/or electronic device 42 may also be programmed or set to indicate various treatment parameters (e.g., the initiation of treatment, warming of the heating elements, completion of treatment, errors, battery life, etc.) through any number of visual, auditory, or haptic indicators.

Additionally, the controller 40 and/or electronic device 42 may be used to store and/or transmit various data such as historical treatment data, usage time, total treatment time, temperature data, etc. Furthermore, the controller 40 and/or electronic device 42 may communicate wirelessly with a remote server or additional controller, allowing the controller 40 and/or electronic device 42 to also be programmed remotely, e.g., by a physician or other party. In yet other variations, audio and/or visual information (e.g., advertisements, educational media, social media connectivity, or other media) may also be displayed upon the controller 40 and/or electronic device 42 which may be received from remote servers or various other data may be transmitted to and/or from the controller 40 and/or electronic device 42 as well.

In yet other variations, although controller 40 is illustrated as being coupled to assemblies 32, 34 via a wired connecting cable 38, other variations may have controller 40 wirelessly connected with assemblies 32, 34. Such a connection may be through any number of wireless protocols such as Bluetooth®, RF, etc.

This "precision temperature control" mobile heating therapy system may be used for heating other parts of the body as well, where the system remains nearly the same, but the heating element dimensions may be varied and power requirements may also be changed depending on the total surface area being treated, temperature goals, patient comfort, or other situational specifics.

With the incorporation of a processor into the treatment strips, treatment times or other parameters such as temperature of the strips may be programmed and optionally shut on or off selectively by the patient or automatically. Moreover, other parameters such as the frequency of the heat delivery or other stimulation may also be programmed by the processor to provide further flexibility in treatment.

Figure 4:
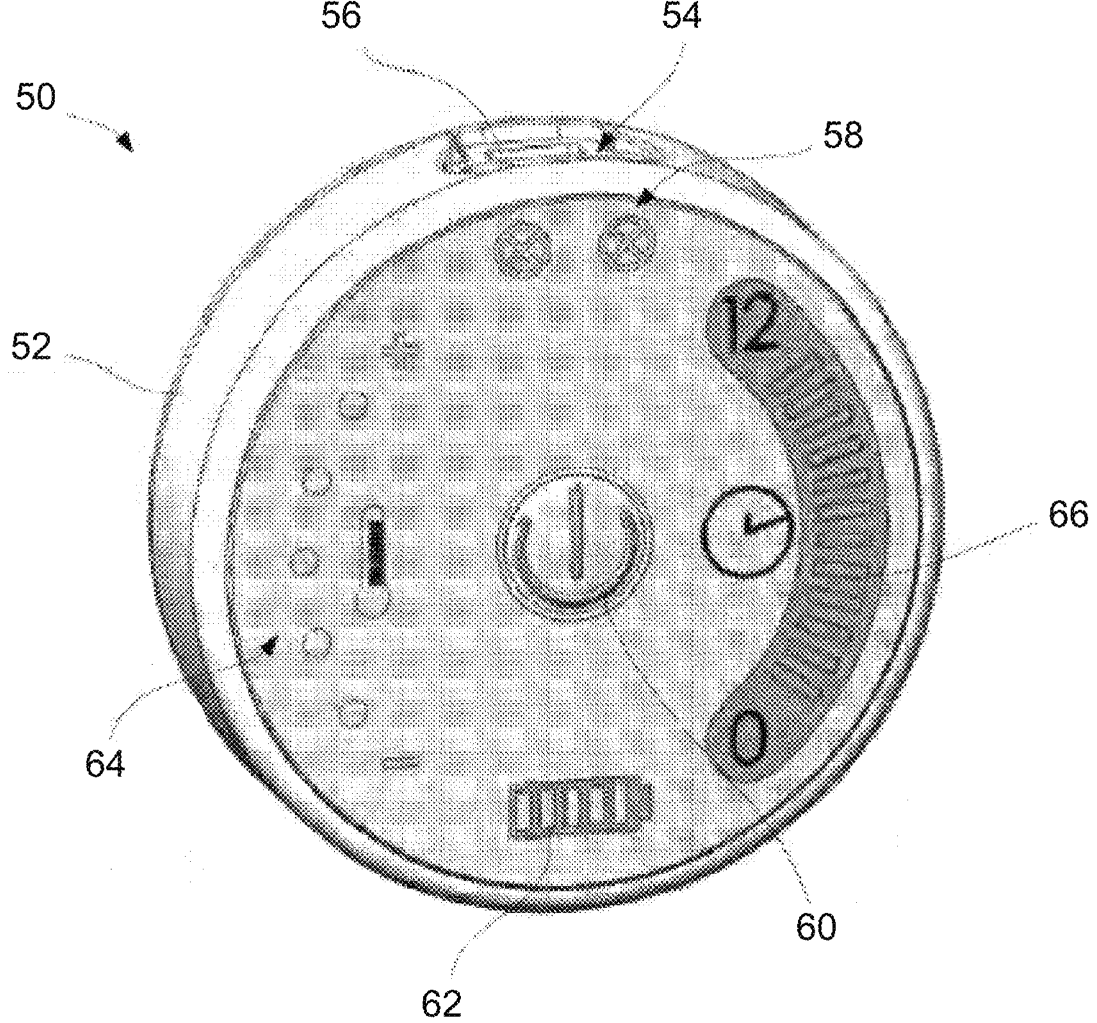
FIG. 4 shows a perspective view of a controller which is specifically designed and programmed for use with the treatment strip assemblies.

In yet another variation, the treatment strip assemblies may be used with a controller 50 which is specifically designed and programmed for use with the treatment strip assemblies. An example of such a controller 50 is shown in the perspective view of FIG. 4 which illustrates the controller 50 which may comprise a housing 52, e.g., a circularly-shaped housing which may weigh less (or more) than 8 ounces, which encloses the power supply and controller board having a programmable processor contained within. The controller housing 52 may incorporate two ports 54 for plugging two heater assemblies, i.e., a first port for connecting a first treatment assembly for the first eye and a second port for connecting a second treatment assembly for the second eye, although in other variations, a single port may be used for treating a single eye. In cases where the tissues around only the first eye are treated, a single port may be utilized. Connector indicators 58 may be included to provide a visual indicator (and/or auditory indicator) to indicate to the user whether the first and/or second ports 54 have heaters properly connected. A charging port 56 for connecting to a power supply for charging the controller 50 may also be incorporated into the housing 52. Ports for heater assemblies 54 on the controller may be oriented relative to the charging port 56 such that charging is not possible with any number of heaters connected to the controller.

A power button 60 may be provided to allow the user to activate the controller 50 on/off and a power indicator 62 may also be provided to show the power level of controller 50. In addition to the power indicator 62, a temperature controller 64 may also be provided to allow for the user to adjust the temperature of the strip assemblies during treatment, e.g., by pressing the "+" or "−" as appropriate. Additionally, a timer 66 may also be provided to give feedback like a visual (and/or auditory) countdown of the treatment time. For instance, when a 15 minute timer has been initiated, each indicator bar of the timer 66 may pulse for 1 min then turn off until the entire 15 minute treatment time has elapsed.

Figure 5A:
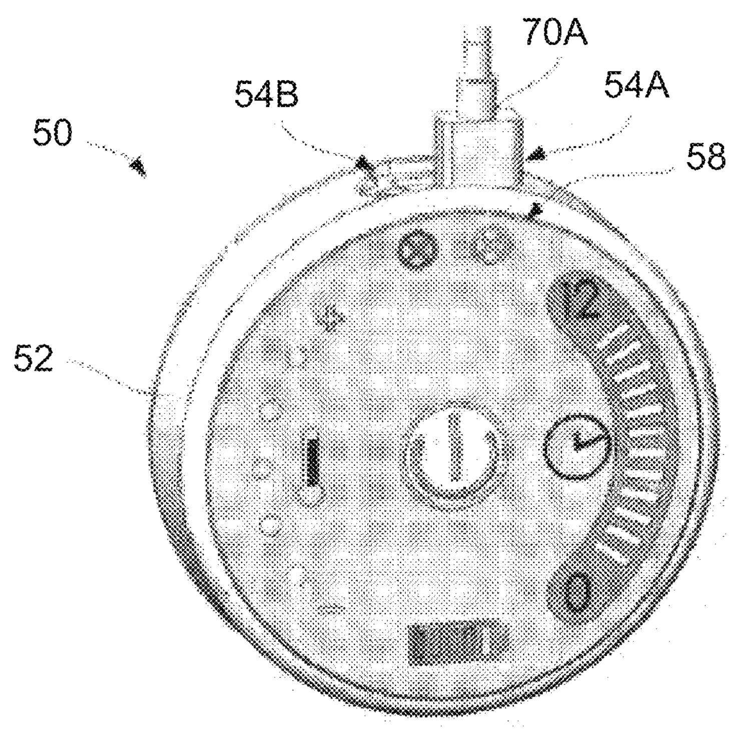
FIGS. 5A and 5B show perspective views of the controller having connectors for respective treatment strip assemblies coupled to the controller.
Figure 5B:
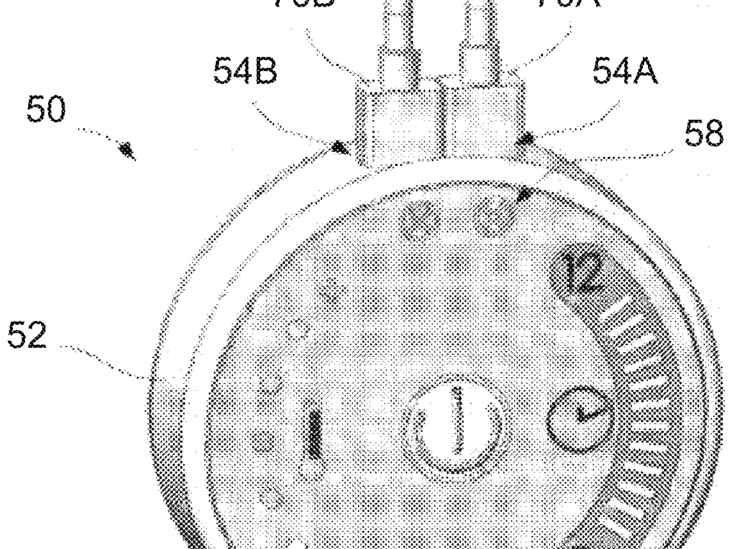

As shown in the perspective views of FIGS. 5A and 5B, the controller 50 may provide a visual indication, as indicated by the connector indicators 58, of when the first connector 70A for the first treatment strip assembly has been inserted into the first port 54A and likewise when the second connector 70B for the second treatment strip assembly has been inserted into the second port 54B.

Figure 6:
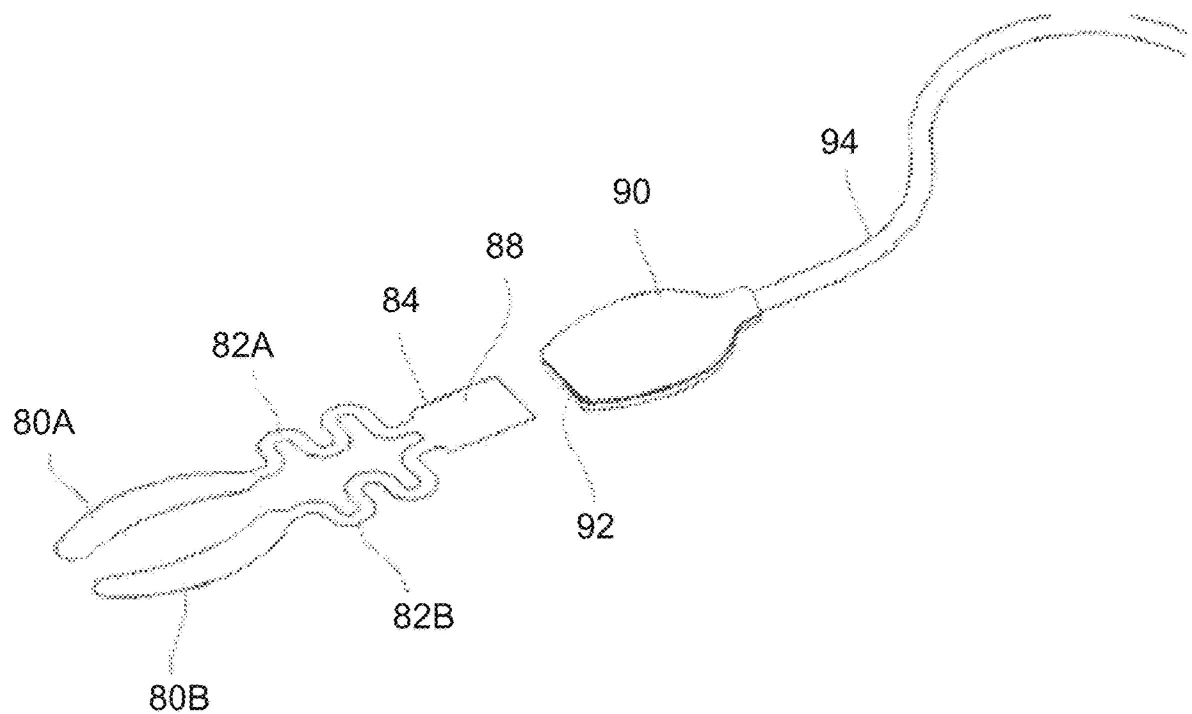
FIG. 6 shows the mating connection of a treatment strip assembly to a re-usable cable assembly.

With respect to the treatment strip assemblies, another variation is shown in the perspective view of FIG. 6 which illustrates heating strips 80A, 80B (which may be applied to the upper lid UL and lower lid LL) which are coupled via respective connectors 82A, 82B (e.g., flexible connectors to accommodate the positioning of the heating strips 80A, 80B to the patient) to a common junction 84 coupling the heating strips 80A, 80B. The junction 84 may be connected to a coupler 90 having a receiving port 92 which is sized to removably receive the junction 84. The coupler 90 may be connected to a cable 94 (e.g., which may be several feet in length to reach from patient's eyes to the controller 350 when located on the wrist) which is then coupled to the port 54A or 54B.

Because the treatment strip assemblies may be designed for single use, the treatment strips may be marked or otherwise electronically tagged (such as via junction 84 or some other indicator) to prevent their re-use by the controller board when previously used treatment strips are connected to the controller 350. In one variation, the junction 84 may incorporate a usage tracking mechanism 88 such as a memory chip that may be programmed to have a "0" or "1" memory which may indicate to the controller board that the particular treatment strip assembly has previously been used, as shown in the detail perspective view of FIG. 7A. In another variation, the usage tracking mechanism 88 may comprise a sacrificial fuse located on the junction 84. A short burst of high energy may be delivered by the controller to the mechanism 88 to blow the fuse. Then the energy for treatment may be lowered by the controller to deliver the proper temperature therapy. Optionally, once the treatment strip assembly has been used, the junction 84 may be removed from receiving port 92 and another junction for a new treatment strip assembly may be inserted for another treatment or for another patient.

In other variations, rather than having a wired connection, the treatment strips may incorporate an antenna and transmitter and/or receiver for communicating wirelessly with the controller board.

Figure 7A:
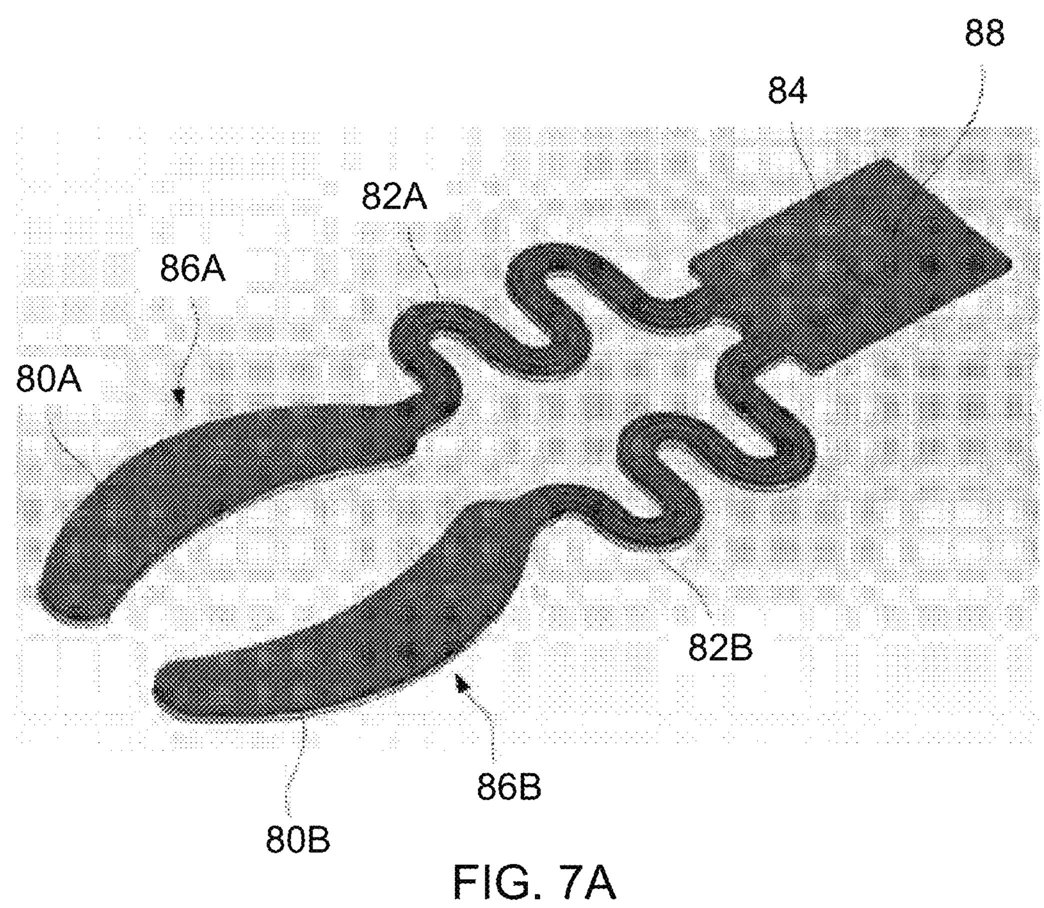
FIG. 7A shows a perspective view of treatment strip assembly coupled via respective connectors to a common junction for attachment to a cable.
Figure 7B:
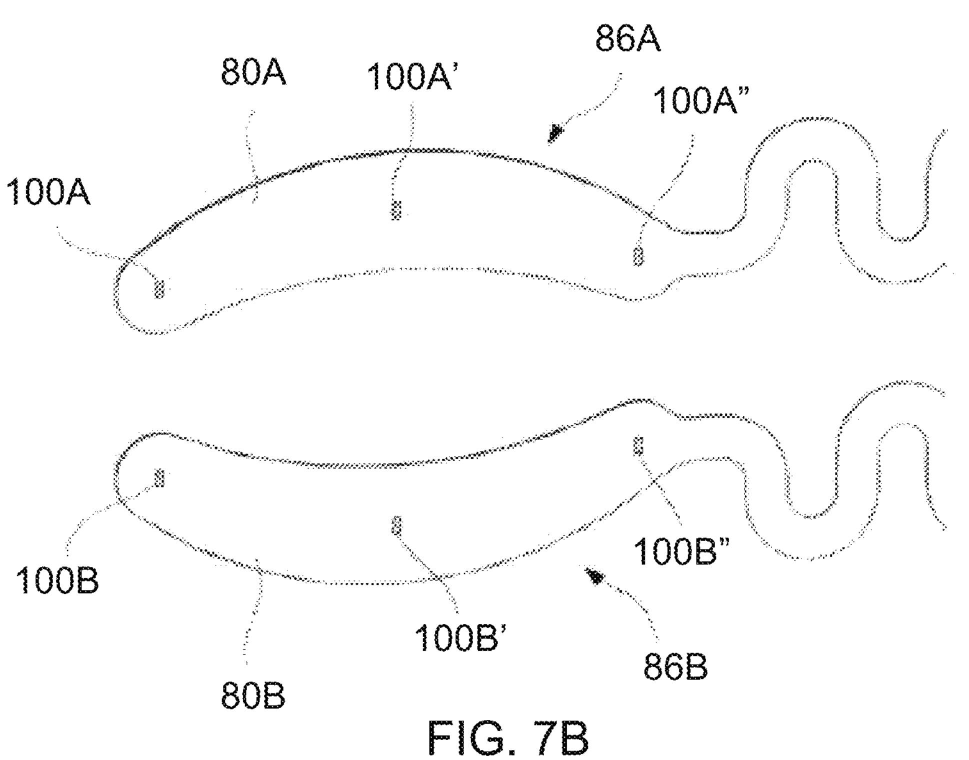
FIG. 7B shows a perspective view of a treatment strip with a sensing layer exposed, illustrating the positions of various sensors.

Each of the heating strips 80A, 80B may include one or more respective sensors 86A, 86B, e.g., thermistors or thermocouples, which may be coupled to a common wire connector or separate wires and positioned upon the strips to provide treatment feedback to the controller board 382 for each eyelid strip, as also shown in FIG. 7A. Each of the heating strips 80A, 80B, for instance, may incorporate anywhere from 1-4 temperature sensors on each strip, e.g., one sensor positioned on a first end, a second sensor positioned on the middle, and a third sensor positioned on a second end of the strip. FIG. 7B shows a top view of the heating strips 80A, 80B illustrating how each strip may incorporate one or more sensors. As shown, the first strip 80A may have a first sensor 100A positioned near or at a first end such as a distal end of the strip, a second sensor 100A' positioned mid-way along the strip, and a third sensor 100A" positioned near or at a second end such as the proximal end of the strip. Likewise with the second strip 80B, a first sensor 100B may be positioned near or at a first end such as a distal end of the strip, a second sensor 100B' may be positioned mid-way along the strip, and a third sensor 100B" may be positioned near or at a second end such as the proximal end of the strip.

An additional temperature sensor may also be placed upon or in proximity to the patient body, e.g., near the patient's temple, upon an additional treatment strip and away from the treatment strips placed upon the patient's eyelids to measure and monitor an ambient temperature where the patient is being treated. This separate ambient temperature data may help to ensure that the treatment strips themselves are working properly and delivering the targeted temperature therapy. Sensors may be used in a comparative mode to determine if any portion of the treatment strip is not in contact with the patient or is malfunctioning.

As described above, the meibomian glands may be mechanically pressed or squeezed to express solidified meibum from the glands in order to help treat MGD. Forceps are typically used to apply pressure upon the meibomian glands. Aside from treating MGD, the forceps may also be used to treat other conditions such as acne, arthralgia, myalgia, hordeolum, styes, chalazion, abcesses, other dermatological conditions, etc. The forceps may also be used for dental applications such as curing adhesives, fillings, etc. Additionally, the forceps may be used for other medical purposes such as tissue ablation, maintaining hemostasis, etc. as well as non-medical purposes such as welding-type applications.

Figure 8:
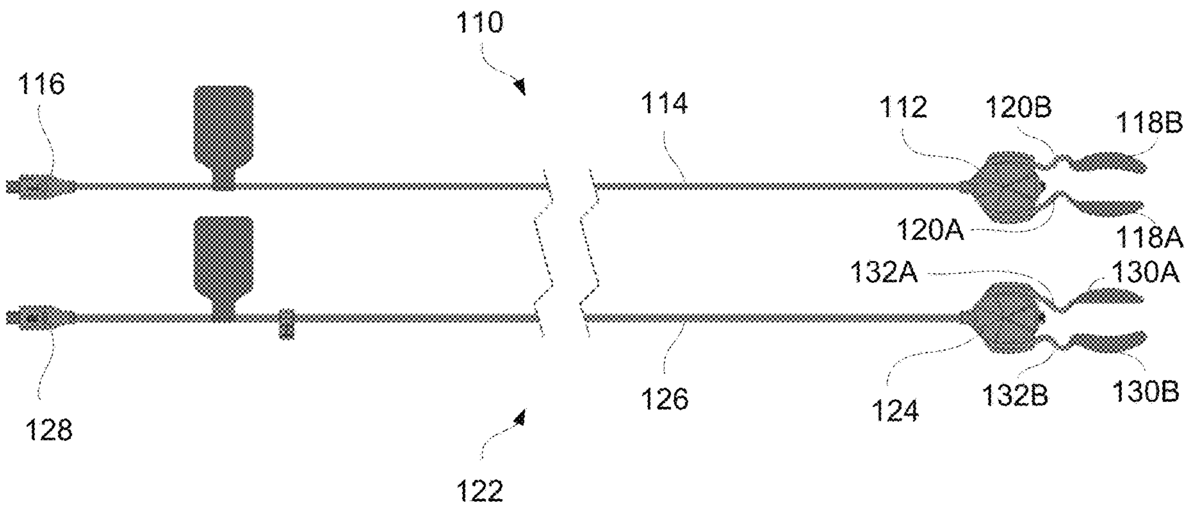
FIG. 8 shows a top view of another variation of treatment strip assemblies for both eyes of a user.

In yet another variation of the treatment strip assembly, FIG. 8 shows a top view of two treatment strip assemblies 110, 122 which may be used to treat one or both eye regions of a patient. The first assembly 110 shows a coupler 112 attached via a cable 114 to a connector 116 which may be connected to any of the controllers described herein. The coupler 112 may be connected to an upper heating strip 118A and a lower heating strip 118B for treating respective upper and lower eyelids of the patient's eye, e.g., patient's left eye. The upper and lower heating strips 118A, 118B may be attached to the coupler 112 via respective flexible connectors 120A, 120B which may be configured to incorporate a stress-relieve portion to accommodate variable positioning of the heating strips relative to the patient when the coupler 112 is attached or otherwise adhered to the patient's skin, such as at or in proximity to the patient's temple for attaching the upper and lower heating strips 118A, 118B to the patient's eyelids.

The second assembly 122 may likewise include a coupler 124 attached via a cable 126 to a connector 128 which may be connected to any of the controllers described herein. The coupler 124 may be connected to an upper heating strip 130A and a lower heating strip 130B for treating respective upper and lower eyelids of the patient's eye, e.g., patient's right eye. Although two assemblies 110, 122 are shown, the system may optionally utilize a single assembly 110 or 122 or both assemblies 110, 122. Moreover, one or both assemblies may utilize a single heating strip or both heating strips in any number of combinations, e.g., single assembly with single heating strip (upper or lower heating strip), single assembly with both heating strips, both assemblies each with a single heating strip (upper or lower heating strip), both assemblies each with both heating strips, etc. where an upper and/or lower heating strip may be used in any number of combinations as needed or desired.

FIG. 9A shows a top view of a coupler 124 having a platform 134 on a first side which may serve as an attachment surface to the patient's skin in proximity to the eye for positioning the upper strip 130A and/or lower strip 130B extending from the couple 124 via flexible connectors 132A, 132B. Each of the flexible connectors 132A, 132B may define a curved or arcuate portion which functions as a stress-relief section to accommodate movement of the strips 130A, 130B relative to the coupler 124 when each of the strips 130A, 130B and coupler 124 are adhered to their relative skin surfaces thereby allowing for the patient to continue blinking of their eyelids in comfort while the strips 130A, 130B and coupler 124 remained adhered to the skin.

FIGS. 9B and 9C show cross-sectional and exploded cross-sectional end views of, e.g., lower strip 130B from FIG. 9A, to illustrate one variation for each of the different layers within the heating strip. A substrate such as a flexible printed circuit board assembly (FPCBA) 140 having one or more heating elements (e.g., resistive heating elements) incorporated throughout the FPCBA layer 140 may be positioned to contact the skin surface of the eyelid under treatment. An adhesive layer 142 may attach the FPCBA layer 140 to a ductile layer 144 which may serve different functions. The ductile layer 144 may be configured to conform to the anatomy of the underlying tissue surface upon which the heating strip is adhered to enable the strip to conform closely to the tissue surface. Once the ductile layer 144 has conformed, it may retain its shape through the course of the treatment to facilitate conductive heat transfer to the tissue and also to increase comfort to the user. Furthermore, the ductile layer 144 may conduct the heat emitted from the FPCBA layer 140 evenly over the entire heating strip assembly to facilitate the treatment of the underlying tissue surface. Hence, to provide the flexibility and structural support to retain a conformed shape as well as to provide efficient heat conduction throughout the heating strip, the ductile layer 144 may be fabricated from, e.g., a metallic material or metallic alloy material, e.g., copper, aluminum, nickel, gold, etc. The thickness of the ductile layer 144 may also be varied depending upon the material used as properties such as conductivity and yield strength will vary between the various material types utilized.

An additional insulating layer 146 (e.g., electrically insulating layer) may be provided adjacent to the ductile layer 144 and an outermost layer such as a foam layer 148 may be provided to ensure that the heat generated by the underlying substrate layer is retained or directed inwardly toward the eyelid skin and tissue rather than being dissipated into the environment. Each of the layers provided may be assembled such that the heating strip presents a flush and smooth surface without any projections which may injure or irritate the contacted tissue skin surface.

Figure 10:
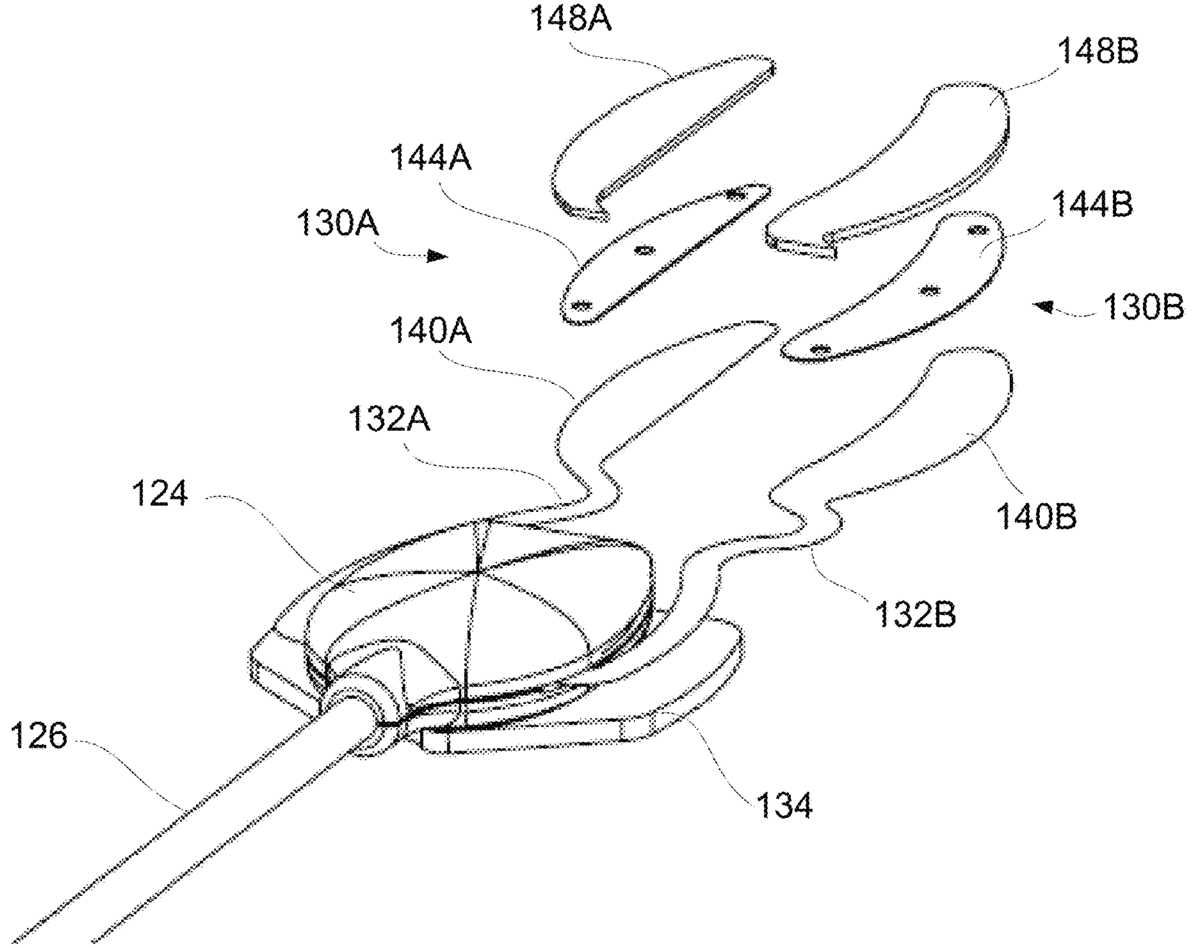
FIG. 10 shows a perspective assembly view of a treatment strip assembly illustrating some of the various layers.

FIG. 10 shows a perspective exploded assembly view of the heating strip assembly, e.g., heating strips 130A, 130B to illustrate a variation of the assembly. As shown, the FPCBA layers 140A, 140B may extend from flexible connectors 132A, 132B and may be formed from the same substrate material, e.g., polyimide. The integrated heating elements may be integrated along the FPCBA layers 140A, 140B. The ductile layers 144A, 144B may be shaped to have the same or similar contours and may further define one or more openings through the layers 144A, 144B through which each of the layers may be attached to one another. The foam layers 148A, 148B may be positioned upon the ductile layers 144A, 144B, as described above, and may also be shaped to have the same or similar contours as the underlying layers. While the ductile layers 144A, 144B are formed as a single layer within each heating strip, the ability of these layers 144A, 144B to conform and retain its shape to the underlying tissue anatomy helps each of the layers of the entire heating strip to likewise conform and retain its shape.

FIG. 11A similarly shows each of the layers (e.g., FPCBA layer 140A, ductile layer 144A, foam layer 148A) of an upper heating strip for treating an upper eyelid positioned adjacent to one another and each having a similar or same contoured shape. The ductile layer 144A is shown positioned between the FPCBA layer 140A and foam layer 148A although in other variations, the order of the layers may be varied. Each of the layers may also have one or more openings, e.g., three openings, defined along the layer at either end and at a central portion to provide for layer alignment and attachment.

FIGS. 11B and 11C show top and end views of one variation of an upper ductile layer 144A. In this variation, the ductile layer 144A may be made of copper although other variations of the layer 144A may utilize other conductive materials. The ductile layer 144A of the upper heating strip may be dimensioned as shown although the dimensions are illustrative. Other variations may be dimensioned differently depending upon the anatomy of the patient or other factors. For instance, the strips may be configured into multiple sizes for different patient types (e.g., pediatric, adult, male, female, etc.) and/or the strips may be dimensioned into different standardized sizes (e.g., small, medium, large, etc.) for each particular patient type, if so desired. Alternatively, different sized heating strips may be utilized between a first and second heating strip assembly used for a single patient depending upon anatomical differences. Moreover, each of the layers and the heating strip assemblies may be similarly or identically dimensioned for placement upon the upper eyelid.

As illustrated, the ductile layer 144A (and/or upper heating strip) may be sized to have a relatively straight distal boundary or edge 176 which may align with or in proximity to the free margin of the upper eyelid. The proximal boundary or edge 178 may be curved and shaped, as shown, to follow a location of the one or more meibomian glands contained within the region of underlying skin in the upper eyelid such that the ductile layer 144A overlays the underlying meibomian glands. Each of the following dimensions are presented as exemplary and may be varied. Furthermore, each of the dimensions may lie in a range within a tolerance of, e.g., ±0.005 in.

The strip may have an overall width 150, e.g., 1.147 in., and an overall height 152, e.g., 0.216 in. The ductile layer 144A may be formed to have one or more openings defined through the layer, as described herein, having a width to a central opening 154, e.g., 0.570 in., a width to first lateral opening 156, e.g., 0.450 in., and a width to second lateral opening 158, e.g., 0.477 in., on either side of the central opening. A height to the central opening 160 may be, e.g., 0.113 in., from the distal edge 176 and a height to the first lateral opening 162 may be, e.g., 0.078 in., and a height to the second lateral opening 164 may be, e.g., 0.072 in. The opening diameter 166 may be, e.g., 0.050 in. diameter, for each of the openings. The proximal edge or boundary 168 may have a radius of, e.g., 1.10 in., which curves radially relative to the distal edge or boundary 176. A first radiused lateral edge 170 may have a radius of, e.g., 0.04 in., and a second radiused lateral edge 172 may also have a radius of, e.g., 0.04 in. The overall thickness 174 of the layer may be, e.g., 0.0058 in.

Figure 12A:
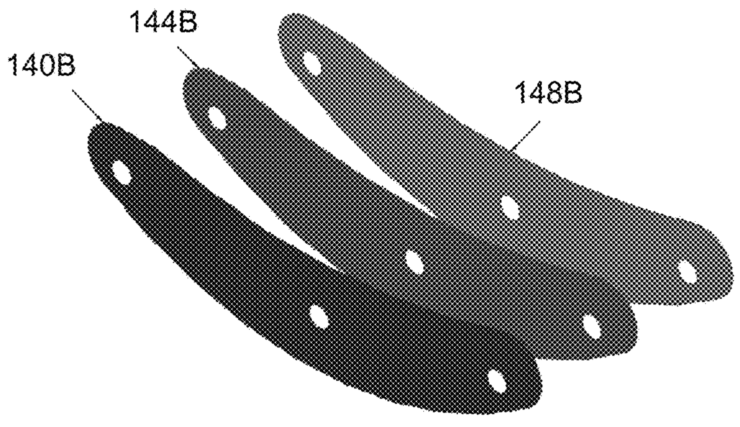
FIG. 12A shows a perspective assembly view of some of the layers of the treatment strip assembly configured for a lower eyelid.

FIG. 12A similarly shows each of the layers (e.g., FPCBA layer 140B, ductile layer 144B, foam layer 148B) of a lower heating strip for treating a lower eyelid positioned adjacent to one another and each having a similar or same contoured shape. The ductile layer 144B is shown positioned between the FPCBA layer 140B and foam layer 148B although in other variations, the order of the layers may be varied. Each of the layers may also have one or more openings, e.g., three openings, defined along the layer at either end and at a central portion to provide for layer alignment and attachment.

Figure 12B:
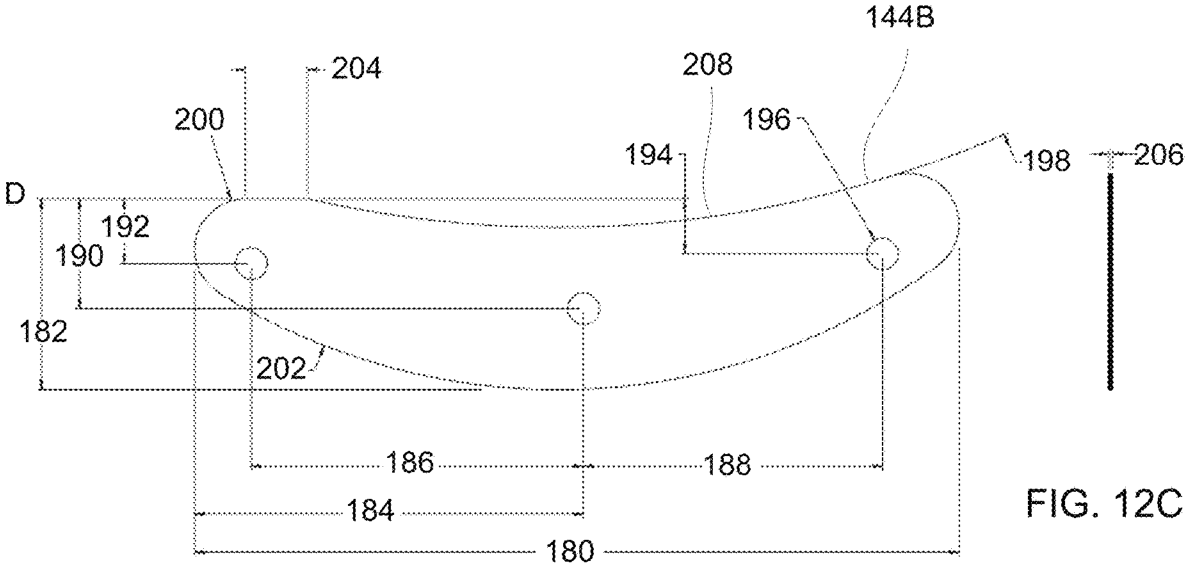

FIGS. 12B and 12C show top and end views of one variation of a lower ductile layer 144B. In this variation, the ductile layer 144B may be made of copper although other variations of the layer 144B may utilize other conductive materials, as described above similarly for the upper ductile layer 144A. The ductile layer 144B of the upper heating strip may be dimensioned as shown although the dimensions are illustrative. Other variations may be dimensioned differently depending upon the anatomy of the patient or other factors. For instance, the strips may be configured into multiple sizes for different patient types (e.g., pediatric, adult, male, female, etc.) and/or the strips may be dimensioned into different standardized sizes (e.g., small, medium, large, etc.) for each particular patient type, if so desired. Alternatively, different sized heating strips may be utilized between a first and second heating strip assembly used for a single patient depending upon anatomical differences. Moreover, each of the layers and the heating strip assemblies may be similarly or identically dimensioned for placement upon the upper eyelid.

As illustrated, the ductile layer 144B (and/or lower heating strip) may be sized to have a curved proximal boundary or edge 208 which may align with or in proximity to the free margin of the lower eyelid. The distal boundary or edge 202 may be curved and shaped, as shown, to follow a location of the one or more meibomian glands contained within the region of underlying skin in the lower eyelid such that the ductile layer 144B overlays the underlying meibomian glands. Each of the following dimensions are presented as exemplary and may be varied. Furthermore, each of the dimensions may lie in a range within a tolerance of, e.g., ±0.005 in.

The strip may have an overall width 180, e.g., 1.201 in., and an overall height 182, e.g., 0.300 in. The ductile layer 144B may be formed to have one or more openings defined through the layer, as described herein, having a width to a central opening 184, e.g., 0.611 in., a width to first lateral opening 186, e.g., 0.522 in., and a width to second lateral opening 188, e.g., 0.470 in., on either side of the central opening. A height to the central opening 190 may be, e.g., 0.173 in., from a datum D of the proximal edge 208 and a height to the first lateral opening 192 relative to the datum D may be, e.g., 0.102 in., and a height to the second lateral opening 194 relative to the datum D may be, e.g., 0.087 in. The opening diameter 196 may be, e.g., 0.050 in. diameter, for each of the openings. The proximal edge or boundary 198 may have a radius of, e.g., 1.74 in., which curves similarly relative to the distal edge or boundary 202. A first radiused lateral edge 200 may have a radius of, e.g., 0.08 in., and a radiused distal edge or boundary 202 may also have a radius of, e.g., 1.01 in. The distance between first lateral opening to the proximal radiused edge 204 may be, e.g., 0.097 in., and the overall thickness 174 of the layer may be, e.g., 0.0058 in.

The applications of the devices and methods discussed above are not limited to the treatment of dry eye syndrome but may include any number of further treatment applications. Moreover, such devices and methods may be applied to other treatment sites within the body where acute or chronic inflammation causes a disease or condition. The treatment strips can be accordingly custom-designed to follow the path of the underlying physiology, e.g. custom designed and contoured cooling or heating treatment strips to treat the sinuses and acute or chronic sinusitis, respectively, rhinitis and allergic rhinitis, joint aches and inflammation, arthritis, muscle aches, back pain, headaches, wounds, sports injuries, etc. Modification of the above-described assemblies and methods for carrying out the invention, combinations between different variations as practicable, and variations of aspects of the invention that are obvious to those of skill in the art are intended to be within the scope of the claims.

What is claimed is:

1. A heating strip system, comprising:

a substrate layer having one or more heating elements incorporated;

a flexible connector formed from the substrate layer and configured to extend from the substrate layer;

a ductile layer attached in proximity to the substrate layer and configured to conform and retain a shape of the substrate layer to an anatomy of an underlying region of skin of an eyelid of a subject;

a protective layer attached in proximity to the ductile layer and where the protective layer, ductile layer, and substrate layer each has a contour which is identical to one another, where the ductile layer and the protective layer are coextensive with a treatment portion of the substrate layer to define a peripheral boundary of the treatment portion, and where the flexible connector is further configured to extend beyond the peripheral boundary, and where each layer defines an opening at each end and at a central portion away from a proximal edge and a distal edge such that each opening coincides with one another when each layer is aligned upon one another, and where each layer is assembled into a heating strip such that the heating strip presents a flush and smooth surface configured to adhere to the underlying region of skin and where the heating strip has a flexibility sufficient to accommodate movement of the eyelid to allow for the subject to blink naturally without restriction while conforming and retaining its shape to the underlying region via the ductile layer; and a controller which is programmable for a treatment therapy and which is in communication with the substrate layer via the flexible connector which is configured to transmit electrical energy to the substrate layer which is configured to receive the electrical energy and emit thermal energy for conduction throughout the heating strip via the ductile layer such that the thermal energy is directed inwardly via the protective layer to the underlying region of skin.

2. The system of claim 1 wherein the heating strip has a first periphery which is shaped to extend and follow a border of one or more meibomian glands contained within the underlying region of skin, and the heating strip further has a second periphery which is shaped to extend and follow a free margin of the eyelid.

3. The system of claim 2 wherein the heating strip is configured to adhere to an upper eyelid.

4. The system of claim 3 further comprising a second heating strip in communication with the controller and configured to adhere to a lower eyelid of the subject.

5. The system of claim 4 wherein the heating strip and second heating strip are electrically coupled to one another via a coupler.

6. The system of claim 1 wherein the heating strip comprises a contact surface for placement against the underlying region of skin.

7. The system of claim 1 wherein the controller is programmed to control one or more parameters of the heating strip.

8. The system of claim 7 wherein the one or more parameters comprise a temperature, treatment time, frequency of treatment, or thermal profile of the heating strip.

9. The system of claim 7 wherein the controller is programmed to heat the heating strip to a temperature of between 40° to 50° C.

10. The system of claim 7 wherein the controller is programmed to heat the heating strip to a temperature up to 45° C.

11. The system of claim 7 wherein the controller is programmed to heat the heating strip to a temperature of between 40.5° to 44.5° C.

12. The system of claim 7 wherein the controller is programmed to heat the heating strip to a temperature of between 41.5° to 43.5° C.

13. The system of claim 1 further comprising one or more temperature sensors incorporated into the heating strip for regulating a temperature of the heating strip.

14. The system of claim 1 wherein the controller is programmed to heat the heating strip for at least between 10 minutes and 60 minutes.

15. The system of claim 1 wherein the controller is programmed to heat the heating strip for up to 15 minutes.

16. A method of treating a subject, comprising:

conforming a heating strip to an underlying region of skin of an eyelid of a subject via a ductile layer which conforms and retains its shape within the heating strip such that the heating strip retains a shape of an anatomy of the underlying region of skin, wherein the ductile layer is positioned between a protective layer and a substrate layer and further presents a flush and smooth surface and where the protective layer, ductile layer, and substrate layer each has a contour which is identical to one another, and where the ductile layer and the protective layer are coextensive with a treatment portion of the substrate layer to define a peripheral boundary of the treatment portion, and where each layer defines an opening at each end and at a central portion away from a proximal edge and a distal edge such that the openings coincide with one another when each layer is aligned upon one another;

initiating a treatment with the heating strip via a controller transmitting electrical energy to the substrate layer of the heating strip having one or more heating elements via a flexible connector formed from the substrate layer and configured to extend from the substrate layer, and where the flexible connector is further configured to extend beyond the peripheral boundary of the treatment portion of the substrate layer; and conducting thermal energy from the substrate layer throughout the heating strip via the ductile layer such that the thermal energy is directed inwardly via the protective layer and into the underlying region of skin.

17. The method of claim 16 wherein the heating strip has a flexibility sufficient to accommodate movement of the eyelid to allow for the subject to blink naturally without restriction from the heating strip while covering one or more meibomian glands contained within the eyelid with the heating strip.

18. The method of claim 17 wherein the heating strip has a first periphery which is shaped to extend and follow a border of the one or more meibomian glands contained within the eyelid and a second periphery which is shaped to extend and follow a free margin of the eyelid.

19. The method of claim 16 wherein conforming the heating strip comprises adhering the heating strip to an upper eyelid of the subject.

20. The method of claim 19 further comprising adhering a second strip to a lower eyelid of the subject such that one or more meibomian glands contained within the lower eyelid are covered by the second strip.

21. The method of claim 20 wherein the heating strip and the second strip are electrically coupled to one another.

22. The method of claim 16 wherein initiating the treatment comprises programming the heating strip via the controller attached to the substrate layer.

23. The method of claim 22 wherein programming the heating strip comprises controlling one or more parameters of the heating strip.

24. The method of claim 23 wherein controlling the one or more parameters comprises controlling a temperature, treatment time, frequency of treatment, or thermal profile of the heating strip.

25. The method of claim 23 wherein controlling the one or more parameters comprises heating the heating strip to a temperature of between 40° to 50° C.

26. The method of claim 23 wherein controlling the one or more parameters comprises heating the heating strip to a temperature up to 45° C.

27. The method of claim 23 wherein controlling the one or more parameters comprises heating the heating strip to a temperature of between 40.5° to 44.5° C.

28. The method of claim 23 wherein controlling the one or more parameters comprises heating the heating strip to a temperature of between 41.5° to 43.5° C.

29. The method of claim 16 wherein the method of treating comprises treating one or more conditions selected from the group consisting of dry eye, evaporative dry eye, and Meibomian gland dysfunction.

30. The method of claim 16 wherein the method of treating comprises treating to improve one or more conditions selected from the group consisting of an ocular surface inflammation, degraded tear quality, degraded lipid layer of tears, and shortened tear break up time.

31. The method of claim 16 further comprising monitoring a temperature of the heating strip via one or more temperature sensors incorporated into the heating strip.

32. The method of claim 16 wherein conducting thermal energy comprises heating the heating strip for at least between 10 minutes and 60 minutes.

33. The method of claim 16 wherein conducting thermal energy comprises heating the heating strip for up to 15 minutes.

34. The method of claim 16 wherein the method comprises treating the subject for a condition selected from the group consisting of meibomitis, blepharitis, ocular rosacea, acne, arthralgia, myalgia, hordeolum, styes, chalazion, and abcesses.

35. The method of claim 16 wherein the method comprises treating the subject for a condition selected from the group consisting of conjunctivitis, keratitis, keratopathy, iritis, cyclitis, glaucoma, and cataract.

36. The method of claim 16 wherein the method comprises treating the subject for improving a comfort level for wearing a contact lens.

* * * * *